US009051395B2

(12) United States Patent
Park et al.

(10) Patent No.: US 9,051,395 B2
(45) Date of Patent: Jun. 9, 2015

(54) ALPHA-1 ANTITRYPSIN VARIANT, PREPARATION METHOD THEREOF AND USE THEREOF

(75) Inventors: Soon Jae Park, Daejeon (KR); Hye-Shin Chung, Daejeon (KR); Sang Mee Lee, Daejeon (KR); Ji-Sun Kim, Daejeon (KR)

(73) Assignee: ALTEOGEN, INC., Daejeon (KR)

( * ) Notice: Subject to any disclaimer, the term of this patent is extended or adjusted under 35 U.S.C. 154(b) by 0 days.

(21) Appl. No.: 14/344,468

(22) PCT Filed: Aug. 13, 2012

(86) PCT No.: PCT/KR2012/006441
§ 371 (c)(1),
(2), (4) Date: Mar. 12, 2014

(87) PCT Pub. No.: WO2013/039295
PCT Pub. Date: Mar. 21, 2013

(65) Prior Publication Data
US 2014/0371160 A1 Dec. 18, 2014

(30) Foreign Application Priority Data

Sep. 15, 2011 (KR) .................. 10-2011-0092819
Jun. 1, 2012 (KR) .................. 10-2012-0058998

(51) Int. Cl.
| C07K 14/81 | (2006.01) |
| A61K 39/00 | (2006.01) |
| C07K 5/06 | (2006.01) |
| C07K 14/745 | (2006.01) |
| C07K 14/755 | (2006.01) |
| C07K 14/785 | (2006.01) |
| C07K 14/52 | (2006.01) |
| A61K 38/05 | (2006.01) |
| C07K 9/00 | (2006.01) |
| A61K 35/16 | (2006.01) |
| C07K 14/47 | (2006.01) |
| A61K 38/17 | (2006.01) |
| A61K 38/00 | (2006.01) |

(52) U.S. Cl.
CPC ............ *C07K 14/8125* (2013.01); *A61K 39/00* (2013.01); *C07K 5/06191* (2013.01); *C07K 14/745* (2013.01); *C07K 14/755* (2013.01); *C07K 14/785* (2013.01); *C07K 14/52* (2013.01); *A61K 38/05* (2013.01); *C07K 9/005* (2013.01); *A61K 35/16* (2013.01); *C07K 14/47* (2013.01); *A61K 38/177* (2013.01); *A61K 38/1709* (2013.01); *C07K 2319/00* (2013.01); *A61K 38/00* (2013.01)

(58) Field of Classification Search
None
See application file for complete search history.

(56) References Cited

FOREIGN PATENT DOCUMENTS

| KR | 10-0133252 B1 | 4/1998 | |
| WO | WO 2008151845 A2 * | 12/2008 | ............... C12N 5/00 |
| WO | WO 2010-123290 A2 | 10/2010 | |

OTHER PUBLICATIONS

Alberts et al., "Chap. 12: Intracellular Compartments and Protein Sorting," Molecular Biology of the Cell, 5th Ed., Garland Science, Taylor & Francis Group, pp. 736-738 (2008).*
Alpha-1 Foundation, "Augmentation therapy," available online at http://alpha-1foundation.org/augmentation-therapy/, 7 pages (2014).*
Alpha-1 Foundation, "Alpha-1 and Liver Disease," available online at http://alpha-1foundation.org/alpha-1-and-liver-disease/, 5 pages (2014).*
Alpha-1 Foundation, "Alpha-1 and Lung Disease," available online at http://alpha-1foundation.org/alpha-1-and-lung-disease/, 4 pages (2014).*
Fairbanks, et al., "Liver Disease in Alpha 1-Antitrypsin Deficiency: A Review," Am. J. Gastroenter. 103:2136-2141 (2008).*
Imperiali et al., "Effect of N-linked glycosylation on glycopeptide and glycoprotein structure," Curr. Opin. Chem. Biol. 3:643-649 (1999).*
Wise, R.A., "Alpha-1 Antitrypsin Deficiency," Merck Manual, available online at http://www.merckmanuals.com/home/lung_and_airway_disorders/chronic_obstructive_pulmonary_disease_copd/alpha1-antitrypsin_deficiency.html, (Jul. 2014).*
R.W. Carrell, et al; Structure and variation of human . . . ; Nature, vol. 298; Jul. 1982; pp. 329-334.
M. Brantly, et al; Molecular basis of alpha-1-antitrypsin deficiency; Am. Journal of Medicine; vol. 84(suppl 6A); Jun. 1988; pp. 13-31.
J. Jeppsson, et al; The amino acid substitutions of human . . . ; FEBS Lett; vol. 231, No. 2, Apr. 1988; pp. 327-330.
T. Mega, et al; Studies on the oligosaccharide chains of human . . . ; Journ. Biol. Chem.; vol. 255, No. 9, 1980, pp. 4057-4061.
P.R. Elliott, et al; Wild-type . . . ; J. Mol. Biol.; vol. 275; 1998; pp. 419-425.
K. Beatty, et al; Kinetics of association of serine proteinases with native . . . ; Journ. of Biol. Chem.; vol. 255, No. 9, 1980; pp. 3931-3934.
E. Karnaukhova, et al; Recombinant human alpha-1 proteinase inhibitor . . . ; Amino Acids; vol. 30; 2006; pp. 317-332.
R.I. Garver, Jr., et al; Production of glycosylated physiologically "normal" human . . . ; Proc. Natl. Acad. Sci.; vol. 84; 1987; pp. 1050-1054.
J. Huang, et al; Expression and purification of functional human . . . ; Biotechnol. Prog.; vol. 17, 2001; pp. 126-133.

(Continued)

*Primary Examiner* — James H Alstrum Acevedo
*Assistant Examiner* — Thea D'Ambrosio
(74) *Attorney, Agent, or Firm* — Lucas & Mercanti, LLP

(57) ABSTRACT

A novel alpha-1 antitrypsin variant, a method of preparing the same, and use thereof are provided. The alpha-1 antitrypsin variant has excellent stability in the body and maintains an inhibitory effect on elastase activities because the blood half-life ($t_{1/2}$) and the area under blood drug concentration vs. time curve (AUC) are remarkably increased by adding an N-glycosylation site in animal cells through amino acid mutation between $1^{st}$ and $25^{th}$ positions of the N-terminus of alpha-1 antitrypsin. Therefore, the alpha-1 antitrypsin variant can be useful in preventing or treating alpha-1 antitrypsin deficiency.

7 Claims, 10 Drawing Sheets

(56) References Cited

OTHER PUBLICATIONS

A.M. Cantin, et al; Polyethylene glycol conjugation at . . . ; Am. Journ. Respiratory Cell and Molecular Biology; vol. 27; 2002; pp. 659-665.

S. Elliott, et al; Enhancement of therapeutic protein in vivo . . . ; Nat. Biotechnol., vol. 21; 2003; pp. 414-421.

M. Terashima, et al; Production of functional human . . . ; Appl. Microbiol. Biotechnol.; vol. 52; 1999; pp. 516-523.

A.J. Sytkowski, et al; Protein chemistry and structure: an erythropoietin fusion protein . . . ; J. Biol. Chem.; vol. 274; 1999; pp. 24773-24778.

M.A. Comunale, et al; Linkage specific fucosylation of alpha-1-anitrypsin in liver . . . ; PLoS One; vol. 5; Issue 8; e12419; 2010; pp. 1-9.

V. Blanchard, et al; N-glycosylation and biological activity of recombinant human . . . ; Biotechnology and Bioengineering; vol. 108; No. 9; 2011; pp. 2118-2128.

K. Mills, et al; The underglycosylation of plasma . . . ; Glycobiology, vol. 13; No. 2; 2003; pp. 73-85.

International Search Report dated Dec. 18, 2012.

* cited by examiner

FIG. 2

```
  1  EDPNGDAANK TNTSHHDQDH PTFNKTTPNL TEFAFSLYRQ LAHQSNSTNI
 51  FFSPVSIATA FAMLSNGTKN DTHDEILEGL NFNLTEIPEA QIHEGFQELL
101  RTLNQPDSQL QLTTGNGLFL SEGLKLVDKF LEDVKKLYHS EAFTVNFTDT
151  EEAKKQINDY VEKGTQGKIV DLVKELDNDT VFALVNYIFF KGKWERPFEV
201  NDTEEEDFHV DNVTTVKVPM MKRLGMFNIQ HCKKLSSWVL LMKYLGNATA
251  IFFLPDEGKL QHLENNLTHD IITKFLENED RRSASLHLPK LSITGTYDLK
301  SVLGQLGITK VFSNGADLSG VTEEAPLKLS KAVHKAVLTI DENGTEAAGA
351  MFLEAIPMSI PPEVKFNKPF VFLMIEQNTK SPLFMGKVVN PTQK 394
```

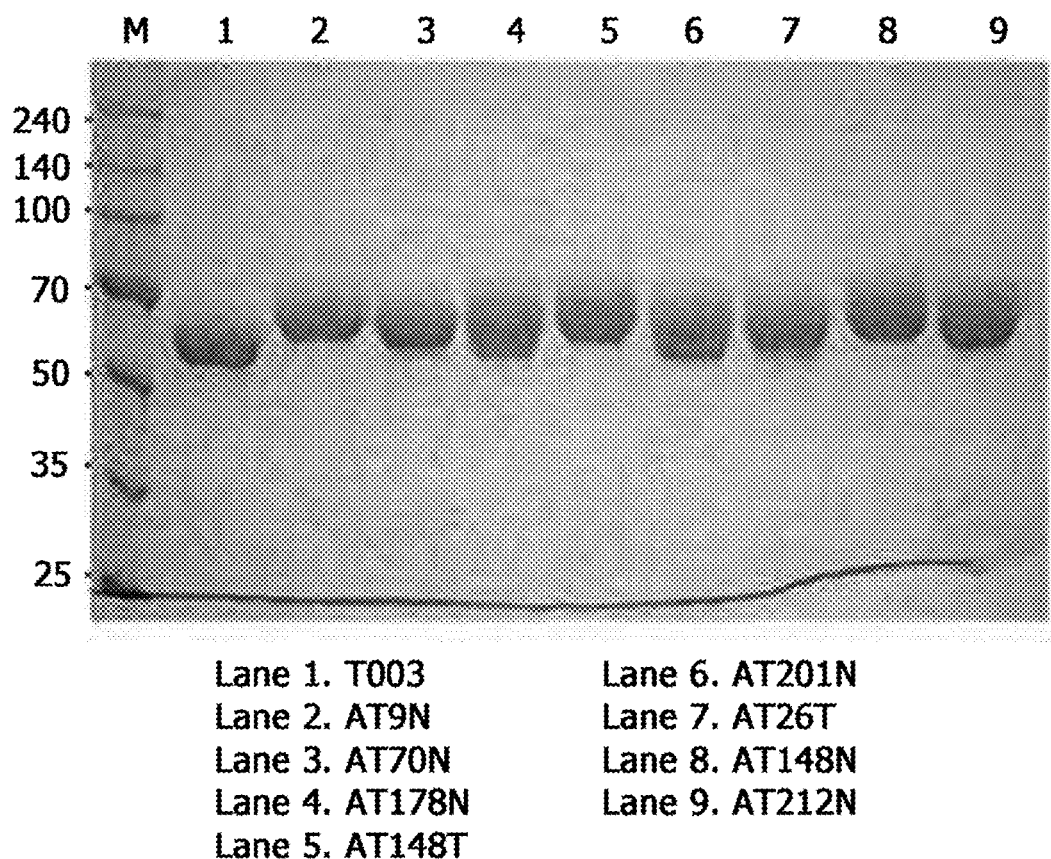

FIG. 7
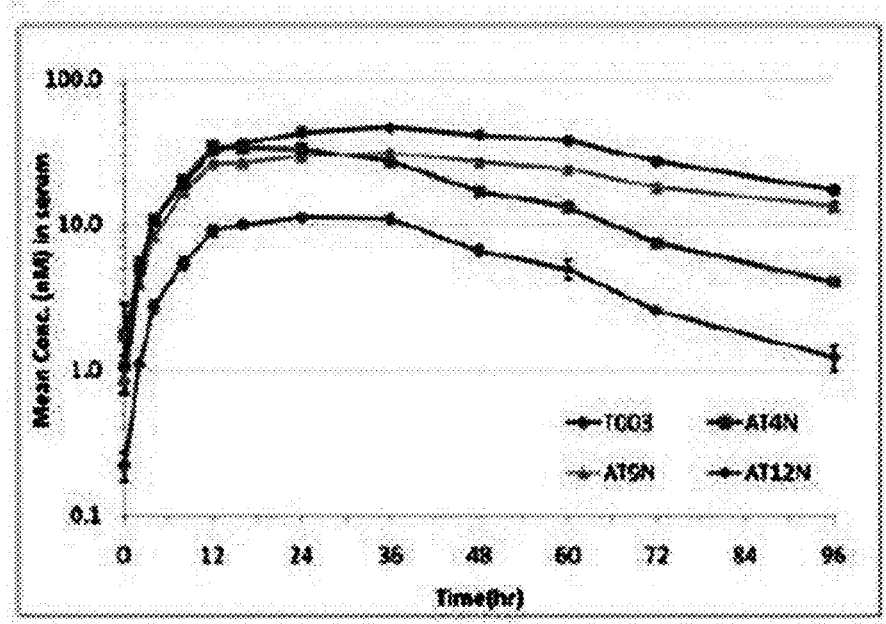
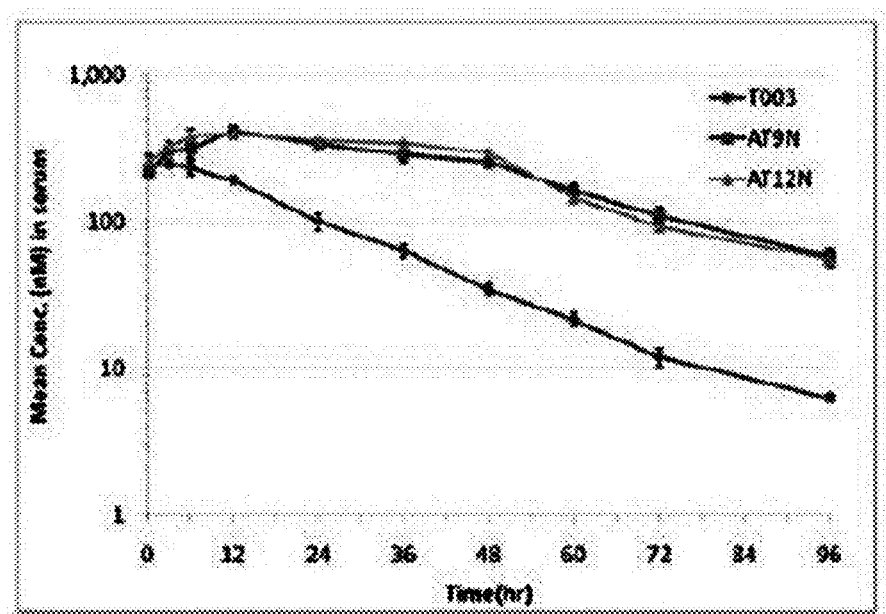

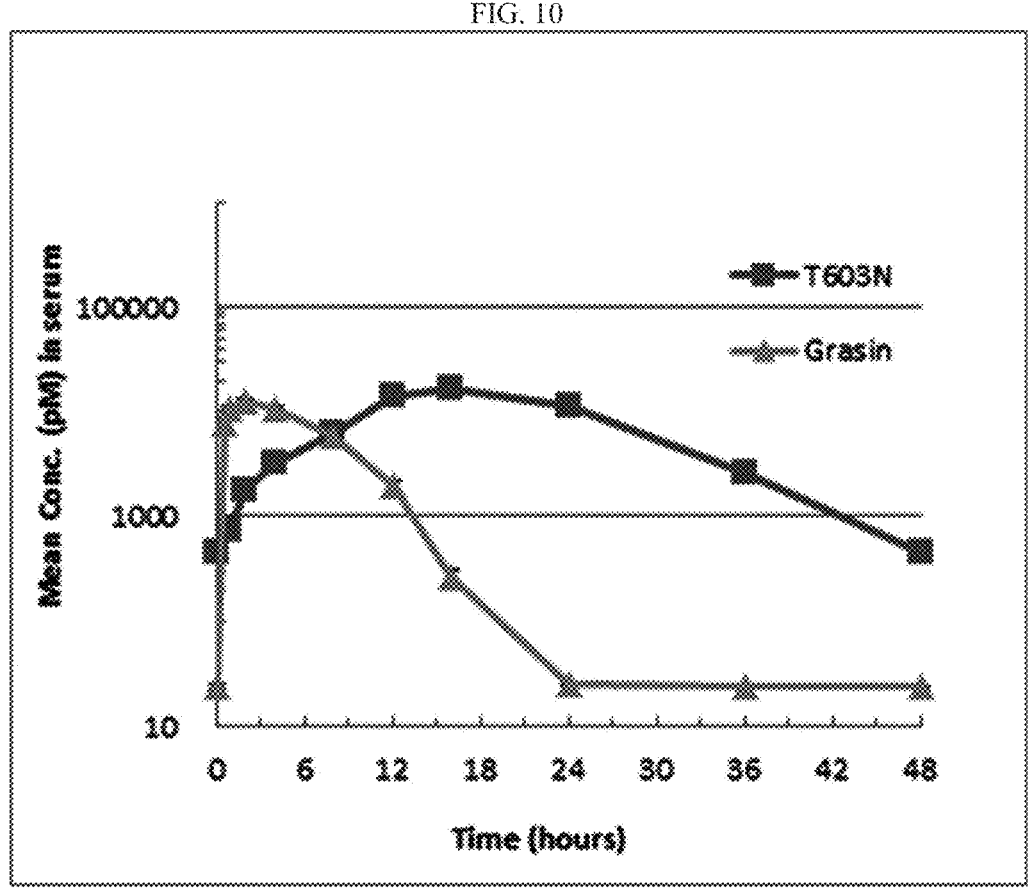

ALPHA-1 ANTITRYPSIN VARIANT, PREPARATION METHOD THEREOF AND USE THEREOF

CROSS-REFERENCE TO RELATED APPLICATIONS

This application is a 371 of PCT/KR2012/006441, filed Aug. 13, 2012, which claims the benefit of Korean Patent Application No. 10-2012-0058998, filed Jun. 1, 2012 and of Korean Patent Application No. 10-2011-0092819, filed Sep. 15, 2011, the contents of each of which are incorporated herein by reference.

TECHNICAL FIELD

The present invention relates to a novel alpha-1 antitrypsin variant, a method of preparing the same, and use thereof.

BACKGROUND ART

Alpha-1 antitrypsin is a protein which is composed of 394 amino acid residues, has a molecular weight of approximately 50,000 daltons (Da), and is present in the blood of mammals. Alpha-1 antitrypsin is one of main blood proteins whose blood concentration amounts to approximately 2 mg/mL (Robin W. C. et. al., Nature, 298, 329-334, 1982), and is also referred to as an alpha-1 protease inhibitor. Alpha-1 antitrypsin has at least about 100 naturally occurring alleles, and its phenotypes are classified into categories A to Z according to the isoelectric focusing (IEF) profiles. Among these, the most abundant M-type allele is known to be present in the blood of most humans and to have at least approximately 75 different isoforms (Brantley, M. et. al., Am. J. Med., 84(suppl. 6A), 13-31, 1988), and maintains a main function as a protease inhibitor.

In general, approximately 90% of alpha-1 antitrypsin isoforms are known to be present as five PiM subtypes such as M1, M2, M3, M4, and M5. Among these, M1, M2 and M3 are distributed at approximately 67%, approximately 16% and approximately 11%, respectively (Jan-Olof Jeppsson and Carl-Bertil Laurell, FEBS Lett., 231, 327-330, 1988). Among these, the M2 and M3 subtypes are known to have histidine (His) and arginine (Arg) at a $101^{st}$ position from the N-terminus, respectively, and these amino acid difference is known to have no effect in innate activities of alpha-1 antitrypsin.

Alpha-1 antitrypsin is a glycoprotein which is glycosylated at 3 sites (Mega, T. et. al., J. Biol. Chem., 255, 4057-4061, 1980). X-ray crystal structure shows that it is composed of 3 beta sheets and 8 alpha helices like other protease inhibitors (serpins) present in blood (Elliot P. R., et. al., JMB, 275, 419-425, 1998). Alpha-1 antitrypsin functions to inhibit various kinds of proteases in the body, and its main in vivo function associated with diseases currently known in the related art is to inhibit neutrophil elastase activities (Beatty et. al., J. Biol. Chem., 255, 3931~3934, 1980). The deficiency of alpha-1 antitrypsin causes severe diseases such as pulmonary emphysema in which pulmonary functions are impaired due to the decomposition of elastin. Also, there is a clinical report showing that modified proteins of alpha-1 antitrypsin are not normally secreted by the liver, but accumulate in the liver, which leads to the onset of hepatocirrhosis.

In recent years, several products extracted from the human blood have been approved by US Food and Drug Administration (FDA), and have been on the market as therapeutic agents to treat alpha-1 antitrypsin deficiency. Representative examples of the products include Prolastin® (commercially available from Talecris Plasma Resources Inc), Aralast™ (commercially available from Baxter Inc), and Zemaira® (commercially available from CSL Behring Inc), which are generally administered at a dose of 60 mg/kg to a human body by intravenous injection at intervals of one week. Therefore, the protein should be administered weekly to an adult patient at a large dose of 4 to 5 g over a long period of time.

According to Data Monitor (DMHC2364) analysis, there are probably 200,000 patients with genetic problems associated with alpha-1 antitrypsin in the US and Europe, but only some of these patients have been treated because proper diagnoses are not made. All the products currently developed as medical purpose are alpha-1 antitrypsin extracted from human blood. Such alpha-1 antitrypsin extracted from human blood may have a risk of including viruses derived from the human body which may cause diseases fatal to humans such as human immunodeficient virus (HIV), hepatitis B virus, or hepatitis C virus, even if it is completely eliminated during a production procedure. Even when alpha-1 antitrypsin is subjected to a blood screening test for the detection of several pathogens and a virus inactivation procedure, it is impossible to eradicate rare pathogens that are not yet known. Therefore, there is always a risk of infection by use blood extracted alpha-1 antitrypsin from unknown pathogens in the human body. Also, the stable supply of uncontaminated blood used to produce a commercially required amount of alpha-1 antitrypsin has been problematic.

As an alternative to solve the aforementioned problems, recombinant DNA technology can be used to develop alpha-1 antitrypsin as a therapeutic agent. Therefore, the recombinant DNA technology has been continuously researched, but there has been no commercially available recombinant alpha-1 antitrypsin yet due to various limiting factors.

Human alpha-1 antitrypsin is known to have 3 N-glycan moieties as it is glycosylated at 3 sites (asparagine at a $46^{th}$ position, asparagine at an $83^{rd}$ position, and asparagine at a $247^{th}$ position). Since alpha-1 antitrypsin produced by a recombinant DNA method using a microorganism such as *E. coli* is not glycosylated, it is known to have a short in vivo half-life when administered to the body (Karnaukhova et. al., Amino Acids, 30, 317-332, 2006, Garver Jr. et. al., Proc. Natl. Acad. Sci. USA., 84, 1050-1054, 1987). To solve this problem and also effectively produce a large amount of alpha-1 antitrypsin, research has been conducted by the expression of alpha-1 antitrypsin in plants. However, it was reported that although the recombinant alpha-1 antitrypsin expressed in plants contained plant-derived glycosylation, it had a shorter half-life in the body than the human alpha-1 antitrypsin (Huang et. al., Biotechnol. Prog., 17, 126-133, 2001).

To increase the half-life of alpha-1 antitrypsin in the body, Cantin et. al. reported a fusion protein by conjugating a polyethylene glycol to a cysteine residue of alpha-1 antitrypsin expressed in microorganisms (Cantin et. al., Am. J. Respir. Cell. Mol. Biol., 27, 659-665, 2002). The article demonstrated that when a polyethylene glycol having a molecular weight of 20 to 40 kDa was conjugated to the cysteine residue of alpha-1 antitrypsin expressed in a microorganism, the conjugated alpha-1 antitrypsin had an increased half-life in the body, compared with the alpha-1 antitrypsin expressed in the microorganism, resulting in the substantially similar half-life to that of the human alpha-1 antitrypsin. However, when a polyethylene glycol is conjugated to a protein, various heterogeneous reaction products can be formed by chemical side reactions. As a result, additional processes are required to remove the heterogeneous reaction products. Also, because there is no N-glycan moieties in a PEG conjugated alpha-1 antitrypsin, this may cause immunogenicity problem by the exposed amino acid sequences when treated for human beings.

Alpha-1 antitrypsin derived from animal cells is known to have substantially the same half-life in the body as human alpha-1 antitrypsin (Garver Jr. et. al., Proc. Natl. Acad. Sci. USA., 84, 1050-1054, 1987). Therefore, a method of producing alpha-1 antitrypsin having a structure similar to the human alpha-1 antitrypsin in animal cells may be preferable. In spite of the advantage of animal cell derived alpha-1 antitrypsin, the production of alpha-1 antitrypsin using the animal cells has a problem in that it is generally more expensive than a method of producing alpha-1 antitrypsin in microorganisms.

Meanwhile, technology of adding a glycosylation site to a loop region of alpha-1 antitrypsin has been suggested to increase the in vivo half-life of alpha-1 antitrypsin. In general, it can be hypothesized that when a protein expressed in animal cells is glycosylated, the protein can be considered to have an increased half-life in the body due to the increased hydrodynamic volume of the glycosylated protein when administered to the human body, compared with the proteins which are not glycosylated. However, as can be seen from examples of erythropoietins, the alteration or addition of a glycosylation site to a physiologically active protein has a great influence on the in vivo half-life of the protein depending on the glycosylation positions (Eliott et. al., Nat. Biotechnol., 21, 414-421, 2003). Therefore, when a glycosylation site is added to alpha-1 antitrypsin in order to increase the in vivo half-life and physiological stability, one has to prove extensively to which position(s) of alpha-1 antitrypsin a glycosylation site is added.

In conclusion, there have been various methods attempted to prepare alpha-1 antitrypsin using recombinant DNA technology in order to enhance in vivo stability of alpha-1 antitrypsin. However, such existing methods are not suitable for the development of alpha-1 antitrypsin as a medicine due to the various problems as described above. Therefore, there is an urgent need for a new method to develop a recombinant alpha-1 antitrypsin having excellent stability in the body.

DISCLOSURE

Technical Problem

To prepare a recombinant alpha-1 antitrypsin having clinical usefulness, the present inventors prepared alpha-1 antitrypsin variants by adding glycosylation sites to alpha-1 antitrypsin at various specific positions, and found that the alpha-1 antitrypsin variant has excellent stability in the body and maintains an inhibitory effect on elastase with remarkable increases in the blood half-life ($t_{1/2}$) and the area under drug blood concentration vs. time curve (AUC). Therefore, the present invention has been completed based on these facts.

Technical Solution

According to an aspect of the present invention, there is provided an alpha-1 antitrypsin variant prepared by substituting an amino acid at a specific site between $1^{st}$ and $25^{th}$ positions of the N-terminus of alpha-1 antitrypsin to add a glycosylation site.

According to one exemplary embodiment of the present invention, the alpha-1 antitrypsin variant may have 1 to 3 glycosylation sites added thereto.

According to another exemplary embodiment of the present invention, the specific site may be present between $3^{rd}$ and $13^{th}$ positions of the N-terminus.

According to still another exemplary embodiment of the present invention, the specific site may be present at a $9^{th}$ or $12^{th}$ position of the N-terminus.

According to yet another exemplary embodiment of the present invention, the specific sites may be present at $4^{th}$ and $9^{th}$ positions, $4^{th}$ and $12^{th}$ positions, or $9^{th}$ and $12^{th}$ positions.

According to another aspect of the present invention, there is provided a method of preparing an alpha-1 antitrypsin variant, which includes substituting an amino acid at a specific site between $1^{st}$ and $25^{th}$ positions of the N-terminus of alpha-1 antitrypsin to add a glycosylation site, culturing cells transformed with an alpha-1 antitrypsin expression vector having the glycosylation site added thereto in a culture medium, expressing an alpha-1 antitrypsin variant protein from the cells, and purifying and recovering the expressed alpha-1 antitrypsin variant protein.

According to still another aspect of the present invention, there is provided a composition for preventing or treating alpha-1 antitrypsin deficiency, which includes an alpha-1 antitrypsin variant as an active ingredient, wherein the alpha-1 antitrypsin variant is prepared by substituting an amino acid at a specific site between $1^{st}$ and $25^{th}$ positions of the N-terminus of alpha-1 antitrypsin to add a glycosylation site.

According to one exemplary embodiment of the present invention, the alpha-1 antitrypsin deficiency may be a chronic obstructive pulmonary disease or hepatocirrhosis.

According to still another aspect of the present invention, there is provided a method of preventing or treating alpha-1 antitrypsin deficiency, which includes administering a therapeutically effective amount of an alpha-1 antitrypsin variant to a patient, wherein the alpha-1 antitrypsin variant is prepared by substituting an amino acid at a specific site between $1^{st}$ and $25^{th}$ positions of the N-terminus of alpha-1 antitrypsin to add a glycosylation site.

According to still another aspect of the present invention, there is provided an alpha-1 antitrypsin variant fusion protein having an increased half-life in the body, wherein the fusion protein is prepared by linking two alpha-1 antitrypsin variants, each of which is prepared by substituting an amino acid at a specific site between $1^{st}$ and $25^{th}$ positions of the N-terminus of alpha-1 antitrypsin to add a glycosylation site.

According to yet another aspect of the present invention, there is provided an alpha-1 antitrypsin variant fusion protein including a heterogeneous protein having an increased half-life in the body, wherein the fusion protein is prepared by linking an alpha-1 antitrypsin variant to the heterogeneous protein, and the alpha-1 antitrypsin variant is prepared by substituting an amino acid at a specific site between $1^{st}$ and $25^{th}$ positions of the N-terminus of alpha-1 antitrypsin to add a glycosylation site.

According to one exemplary embodiment of the present invention, the alpha-1 antitrypsin variant may have an amino acid proline at a $357^{th}$ position, which is a P2 position, further substituted with asparagine.

Advantageous Effects

The alpha-1 antitrypsin variant according to the present invention has excellent stability in the body and maintains an inhibitory effect on elastase activities since the blood half-life ($t_{1/2}$) and the area under blood drug concentration vs. time curve (AUC) are remarkably increased by adding an N-glycosylation site through amino acid mutation between $1^{st}$ and 25th positions of the N-terminus of alpha-1 antitrypsin. Therefore, the alpha-1 antitrypsin variant according to the present invention can be useful in preventing or treating alpha-1 antitrypsin deficiency. Also, the alpha-1 antitrypsin variant according to the present invention can be used to treat alpha-1 antitrypsin deficiency, and can be used to increase the half-life of a heterogeneous protein in the body when the heterogeneous protein is linked to the alpha-1 antitrypsin variant.

DESCRIPTION OF DRAWINGS

These and other features, aspects, and advantages of preferred embodiments of the present invention will be more fully described in the following detailed description and accompanying drawings. In the drawings:

FIG. 2 is a diagram showing sequences and positions of alpha-1 antitrypsin variants according to the present invention;

FIG. 3 is a diagram showing the SDS-PAGE results of purified alpha-1 antitrypsin and variants thereof according to the present invention;

FIG. 7 is a pharmacokinetic graph plotted for alpha-1 antitrypsin variants upon subcutaneous and intravenous administration according to the present invention;

FIG. 10 is a pharmacokinetic graph plotted for a granulocyte colony stimulating factor/alpha-1 antitrypsin variant fusion upon subcutaneous administration according to the present invention.

MODE FOR INVENTION

Figure 1:
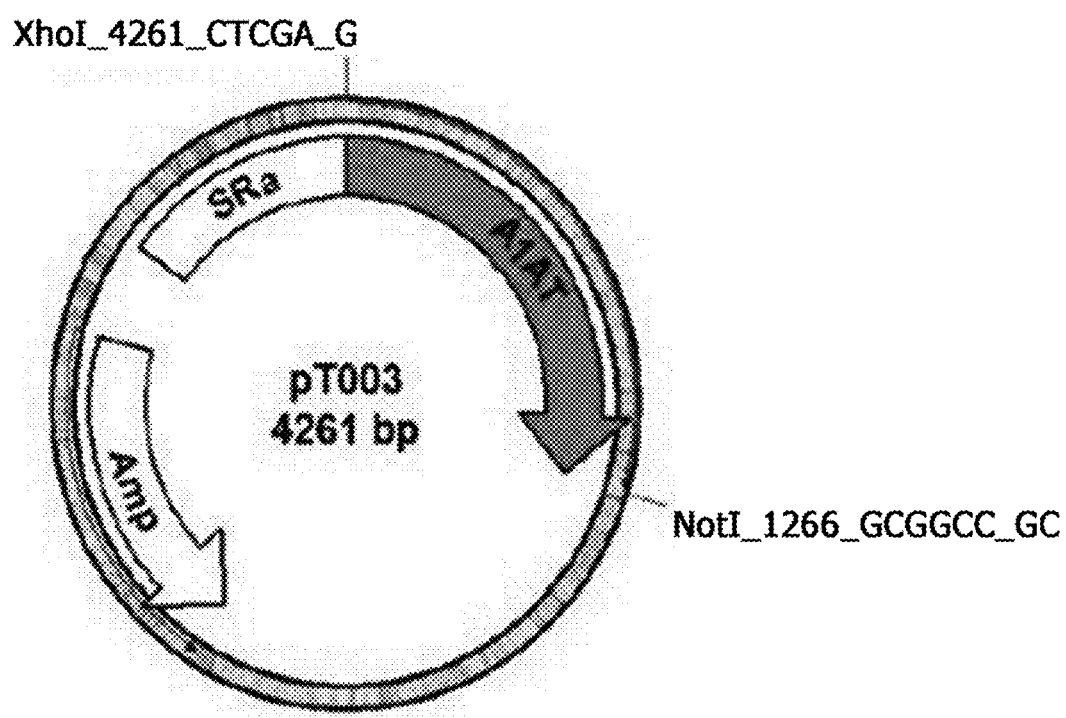
FIG. 1 is a schematic diagram showing an alpha-1 antitrypsin vector (pT003) according to the present invention.

The present invention is directed to an alpha-1 antitrypsin variant prepared by substituting an amino acid at a specific site between $1^{st}$ and $25^{th}$ positions of the N-terminus of alpha-1 antitrypsin to add a glycosylation site.

The alpha-1 antitrypsin variant according to the present invention is characterized in that, in addition to the three glycosylation sites (asparagine at a $46^{th}$ position, asparagine at an $83^{rd}$ position, and asparagine at a $247^{th}$ position) of alpha-1 antitrypsin, an amino acid at a specific site between $1^{st}$ and $25^{th}$ positions of the N-terminus of the alpha-1 antitrypsin is substituted to add an N-glycosylation site. The number of the glycosylation sites to be added is not limited. For example, the number of the glycosylation sites may be in a range of 1 to 3.

Addition of the N-glycosylation site to the specific site of the N-terminus of the human alpha-1 antitrypsin may be performed to form a sequence Asn-X-Thr/Ser which is a sequence coding for an N-glycan attachment site between $1^{st}$ and $25^{th}$ positions of the N-terminus Preferably, glutamine, which is an amino acid present between $3^{rd}$ and $13^{th}$ positions of the N-terminus of the human alpha-1 antitrypsin, and preferably present at a $9^{th}$ or $12^{th}$ position of the N-terminus, is substituted with asparagine to add a glycosylation site. Variants formed by addition of the glycosylation site may have a structure in which sugars are added at $4^{th}$ and $9^{th}$ positions, $4^{th}$ and $12^{th}$ positions, or $9^{th}$ and $12^{th}$ positions. In addition to the specific sites described herein, the alpha-1 antitrypsin variants may be glycosylated at another site within the $25^{th}$ position of the N-terminus.

Also, the present invention is directed to a method of preparing an alpha-1 antitrypsin variant, which includes substituting an amino acid at a specific site between $1^{st}$ and $25^{th}$ positions of the N-terminus of alpha-1 antitrypsin to add a glycosylation site, culturing cells transformed with an alpha-1 antitrypsin expression vector having the glycosylation site added thereto in a culture medium, expressing an alpha-1 antitrypsin variant protein from the culture solution, and purifying and recovering the expressed alpha-1 antitrypsin variant protein.

Recombinant DNA technology may be used as the aforementioned technology of adding an N-glycosylation site, and an amino acid may be substituted, inserted and removed through gene manipulation to add the N-glycosylation site. Approximately 20 amino acids of the N-terminus of the human alpha-1 antitrypsin constitute a region which was not easily detected in the X-ray crystal structure of alpha-1 antitrypsin (PDB code: 1QLP, 2QUG, 3CWL, 1PSI, 7API, 1KCT. In this case, the N-terminal region of alpha-1 antitrypsin had a three-dimensional structure which was very flexible and was not organized.

The alpha-1 antitrypsin variant according to the present invention may be prepared by mutating at least one amino acid using a site-directed mutagenesis method. For example, when glutamine at a $9^{th}$ position of the human alpha-1 antitrypsin is substituted with asparagine or glycine at a $148^{th}$ position is substituted with asparagine, and the modified human alpha-1 antitrypsin is expressed in animal cells, a glycosylation site is formed on the asparagine residue substituted for glutamine ($9^{th}$) or glycine ($148^{th}$). Also, when glycine at a $148^{th}$ position is substituted with threonine, a new glycosylation site is formed on asparagine at a $146^{th}$ position. In this way, glycosylation sites may be added at various positions of the alpha-1 antitrypsin.

In the present invention, an alpha-1 antitrypsin variant is prepared by adding an N-glycosylation site through substitution of the amino acid at the specific site between $1^{st}$ and $25^{th}$ positions of the N-terminus of the human alpha-1 antitrypsin, which was not organized in the X-ray crystal structure of alpha-1 antitrypsin (A1AT), in addition to the three glycosylation sites (asparagine at a $46^{th}$ position, asparagine at an $83^{rd}$ position, and asparagine at a $247^{th}$ position) of the human alpha-1 antitrypsin. Then, the alpha-1 antitrypsin variant is expressed in Chinese hamster ovary cells, and purified with high purity using a chromatography method.

The purified alpha-1 antitrypsin variant having the N-glycosylation site added thereto is observed on a staining band which is run at a relatively higher position than the wild-type alpha-1 antitrypsin in an SDS-PAGE test. This demonstrates that the molecular weight of the alpha-1 antitrypsin variant is increased by glycosylation.

Also, the purified alpha-1 antitrypsin variant has excellent stability in the body due to remarkable increases in the area under blood drug concentration vs. time curve (AUC) and the in vivo half-life ($t_{1/2}$). However, in the case of the variant (I26T) in which the amino acid at the 26$^{th}$ position of alpha-1 antitrypsin is substituted with threonine, in vivo stability was not improved even by addition of the N-glycosylation site. Also, the alpha-1 antitrypsin variants in which a glycosylation site is added to a loop region (loop A, loop B, loop C, loop D, or loop E) as described in WO 2008/151845 or the vicinity of the loop region has no significant effect of improving in vivo stability. In addition, because glycosylation of the loop region may affect the activities of alpha-1 antitrypsin which essentially functions as a protease inhibitor, it is very important to select a glycosylation position which does not affect the alpha-1 antitrypsin activities.

It was also confirmed that the purified alpha-1 antitrypsin variant maintained an inhibitory effect against elastase. In addition, it is known that an association rate constant of the human alpha-1 antitrypsin was generally in a range of $1.0 \pm 0.2 \times 10^5$ (Boudier C., 1994) to $1.67 \times 10^6$ $M^{-1}s^{-1}$ (Terashima M, et. al., Appl. Microbiol. Biotechnol., 52(4), 516-523, 1999). The wild-type human alpha-1 antitrypsin and variants thereof according to the present invention have association rate constants and equilibrium constants similar to those of the human alpha-1 antitrypsin. Therefore, it could be seen that the glycosylation of the N-terminus of alpha-1 antitrypsin did not affect inhibition of the elastase activities.

Also, the present invention is directed to an alpha-1 antitrypsin variant fusion protein having an increased half-life in the body. Here, the fusion protein is prepared by linking the two alpha-1 antitrypsin variants to each other.

The present inventors prepared an alpha-1 antitrypsin double variant in which an amino acid, proline, at a 357$^{th}$ position which was a P2 position of the alpha-1 antitrypsin variant was further substituted with asparagine, prepared a fusion protein in which a granulocyte colony stimulating factor was linked to the double variant of alpha-1 antitrypsin, performed a pharmacokinetic test, and confirmed that the fusion protein had increased stability in the body (see Experimental Example 5). From the results, it could be seen that the in vivo half-life of a heterogeneous protein such as a physiologically active protein was increased when the physiologically active protein was linked to the double variant of alpha-1 antitrypsin.

Therefore, the present invention is directed to an alpha-1 antitrypsin variant fusion protein in which the in vivo half-life of another heterogeneous protein is increased by linking the heterogeneous protein to the alpha-1 antitrypsin variant. The kind of the heterogeneous protein is not limited, but may be a physiologically active peptide or a physiologically active protein.

The alpha-1 antitrypsin variant fusion protein having an increased half-life may be prepared by linking the two or more purified alpha-1 antitrypsin variants. In the previous studies, Sytkowski, A. J. et. al. reported that when erythropoietin (EPO) was linked using a proper linker to prepare an EPO-EPO fusion protein, the fusion protein had remarkably increased activities and longer half-life in the body than an EPO monomer (Sytkowski, A. J., et. al., J. Biol. Chem., 274, 24773-24778, 1999). Therefore, when the two or more alpha-1 antitrypsin variants of the present invention are linked to each other, the half-life of the fusion protein is expected to increase compared to the alpha-1 antitrypsin variant monomer. Further, when a physiologically active peptide or an immune regulatory factor or a cytokine and the like with a short half-life in the body is linked to the alpha-1 antitrypsin variant according to the present invention, the in vivo half-life is expected to be remarkably increased, thereby exhibiting a sufficient stability effect.

Also, the present invention is directed to a composition for preventing or treating alpha-1 antitrypsin deficiency, which includes the alpha-1 antitrypsin variant as an active ingredient.

In addition, the present invention is directed to a method of preventing or treating alpha-1 antitrypsin deficiency, which includes administering a therapeutically effective amount of the alpha-1 antitrypsin variant to a patient.

As described above, the alpha-1 antitrypsin variant according to the present invention has excellent stability in the body and maintains an inhibitory effect against elastase because the blood half-life ($t_{1/2}$) and the area under blood drug concentration vs. time curve (AUC) are remarkably increased by adding an N-glycosylation site through amino acid mutation between 1$^{st}$ and 25$^{th}$ positions of the N-terminus of alpha-1 antitrypsin. Therefore, the alpha-1 antitrypsin variant according to the present invention may be useful in preventing or treating alpha-1 antitrypsin deficiency. The alpha-1 antitrypsin deficiency includes a chronic obstructive pulmonary disease (COPD) or hepatocirrhosis, preferably pulmonary emphysema, but the present invention is not limited thereto.

In addition to the alpha-1 antitrypsin variant, the composition according to the present invention may include at least one known active ingredient having an effect of preventing or treating alpha-1 antitrypsin deficiency.

The composition according to the present invention may be prepared to further include at least one pharmaceutically available carrier in addition to the active ingredient as described above for the purpose of administration. The pharmaceutically available carrier may be used in combination with at least one selected from the group consisting of saline, sterile water, a Ringer's solution, buffered saline, a dextrose solution, a maltodextrin solution, glycerol, ethanol and a mixture thereof. As necessary, another typical additive such as an antioxidant, a buffer and a bacteriostatic agent may be added. Also, a diluent, a dispersing agent, a surfactant, a binder and a lubricant are further added to the composition, which may then be formulated into an injectable formulation, a pill, a capsule, a granule, or a tablet. Further, the composition may be desirably formulated according to diseases or ingredients using a proper method known in the related art, or a method disclosed in Remington's Pharmaceutical Science (the latest version), Mack Publishing Company, Easton Pa.

The composition according to the present invention may be administered orally or parenterally (for example, intravenous, subcutaneous or intraperitoneal injection, inhalation, or local application) according to a desired method, and may be used for gene therapy using the alpha-1 antitrypsin variant according to the present invention. The dose of the composition may vary according to body weight, age, sex, and health condition of a patient, diet, an administration time, a method of administration, a release rate, and severity of a disease. The dose of the alpha-1 antitrypsin variant administered once a week is a dose lower than 60 mg/kg, which is a dose of the alpha-1 antitrypsin, but enables the composition to show substantially the same clinical efficacy. Also, when the alpha-1 antitrypsin variant is administered at the same dose as the wild-type alpha-1 antitrypsin, the composition is expected to show the same clinical efficacy even when the administration duration is further extended.

The composition of the present invention may be used alone or in combination with surgery, hormone therapy, drug treatment, and methods using a biological response modifier.

Hereinafter, preferred Examples and Experimental Examples are provided to aid in understanding the present invention. However, it should be understood that detailed description provided herein is merely intended to provide a better understanding of the present invention, and is not intended to limit the scope of the present invention.

EXAMPLE 1

Preparation of Alpha-1 Antitrypsin and Variant and Dimer Thereof 1-1. Construction of Expression Vector pAV1

A pAV1 vector developed by properly modifying a parent vector, pSGHV0 (GenBank Accession No. AF285183), for the purpose of industrial use was used as an expression vector required for the cloning in the present invention. The parent vector was a laboratory vector constructed to easily purify a protein having physiological activities when a human originated protein was overexpressed at a high concentration and released from animal cells, but did not exhibit activities when the protein was expressed in bacteria such as *E. coli*. However, because the parent vector had various limitations in use for the production in industries, the parent vector was modified to be used in the industries having a high expression level of the protein which is the highest merit of the pSGHV0 vector.

1-2. Construction of Alpha-1 Antitrypsin (Subtype M3) Vector (pT003)

To construct an alpha-1 antitrypsin vector, an alpha-1 antitrypsin vector (pT003) was constructed by cloning an alpha-1 antitrypsin (M3) gene into a pAV1 vector, using hMU001448 (KRIBB) as a template. In detailed description, the hMU001448 (KRIBB) template was amplified by a polymerase chain reaction (PCR) using two primers: XhoAT forward primer (5'-CCC TCC TCG AGA ATG CCG TCT TCT GTC TCG-3', SEQ ID NO: 1) and ATNot reverse primer (5'-GGG CCC GCG GCC GCA GTT ATT TTT GGG TGG G-3', SEQ ID NO: 2). Both ends of the amplified nucleotide were digested with two restriction enzymes XhoI and NotI, and fused with an expression vector pAV1 having an XhoI/NotI restriction site, resulting in the construction of an alpha-1 antitrypsin vector (pT003, SEQ ID NO: 39). This alpha-1 antitrypsin vector (pT003) is schematically shown in FIG. 1.

1-3. Preparation of Alpha-1 Antitrypsin (M3) Variant

To prepare many alpha-1 antitrypsin variants having a glycosylation site added thereto, the alpha-1 antitrypsin vector (pT003) prepared in Example 1-2 was used as a template. Pairs of forward primers and reverse primers listed in the following Table 1, and a mutagenesis kit (Enzynomix, EZchange™ Site-Directed Mutagenesis Kit) were used to prepare alpha-1 antitrypsin variants. The sequences and positions of the alpha-1 antitrypsin variants are shown in FIG. 2.

Because the purpose of mutations of all the alpha-1 antitrypsin variants was to add an N-glycosylation site, an original amino acid was generally substituted with asparagine to form a sequence Asn-X-Thr which was known to be N-glycosylation site in animal cells. In some cases, however, an amino acid adjacent to the asparagine residue was replaced with threonine in order to use an asparagine residue appearing in an original DNA sequence.

TABLE 1

| Primers | Sequences |
| --- | --- |
| Q4N-F (SEQ ID NO: 3) | 5'-AAC GGA ACT GCT GCC CAG AAG ACA GAT ACA-3' |
| Q4N-R (SEQ ID NO: 4) | 5'-GGG ATC CTC AGC CAG GGA GAC-3' |
| Q9N-F (SEQ ID NO: 5) | 5'-AAC AAG ACA GAT ACA TCC CAC-3' |
| Q9N-R (SEQ ID NO: 6) | 5'-GGC AGC ATC TCC CTG GGG ATC-3' |
| D12N-F (SEQ ID NO: 7) | 5'-AAT ACA ACC CAC CAT GAT CAG GAT CAC-3' |
| D12N-R (SEQ ID NO: 8) | 5'-TGT CTT CTG GGC AGC ATC TCC-3' |
| I26T-F (SEQ ID NO: 9) | 5'-ACT ACC CCC AA CCT GGC TG-3' |
| I26T-R (SEQ ID NO: 10) | 5'-CTT GTT GAA GGT TGG GTG ATC C-3' |
| A31T-F (SEQ ID NO: 11) | 5'-ACT GAG TTC GCC TTC AGC CTA TAC-3' |
| A31T-R (SEQ ID NO: 12) | 5'-CAG GTT GGG GGT GAT CTT GTT G-3' |
| L66N-F (SEQ ID NO: 13) | 5'-AAC GGG ACC AAG GCT GAC AC-3' |
| L66N-R (SEQ ID NO: 14) | 5'-GGA GAG CAT TGC AAA GGC TGT A-3' |
| A70N-F (SEQ ID NO: 15) | 5'-AAC GAC ACT CAC GAT GAA ATC CTG-3' |
| A70N-R (SEQ ID NO: 16) | 5'-CTT GGT CCC CAG GGA GAG-3' |
| G148N-F (SEQ ID NO: 17) | 5'-AAC GAC ACC GAA GAG GCC AAG-3' |
| G148N-R (SEQ ID NO: 18) | 5'-GAA GTT GAC AGT GAA GGC TTC TG-3' |
| G148T-F (SEQ ID NO: 19) | 5'-ACT GAC ACC GAA GAG GCC AAG-3' |
| G148T-R (SEQ ID NO: 20) | 5'-GAA GTT GAC AGT GAA GGC TTC TG-3' |
| R178N-F (SEQ ID NO: 21) | 5'-AAC GAC ACA GTT TTT GCT CTG GTG-3' |
| R178N-R (SEQ ID NO: 22) | 5'-GTC AAG CTC CTT GAC CAA ATC CA-3' |

TABLE 1-continued

| Primers | Sequences |
|---|---|
| K201N-F (SEQ ID NO: 23) | 5'-AAC GAC ACC GAG GAA GAG GAC-3' |
| K201N-R (SEQ ID NO: 24) | 5'-GAC TTC AAA GGG TCT CTC CCA TT-3' |
| Q212N-F (SEQ ID NO: 25) | 5'-AAC GTG ACC ACC GTG AAG GTG-3' |
| Q212N-R (SEQ ID NO: 26) | 5'-GTC CAC GTG GAA GTC CTC TTC-3' |
| E266N-F (SEQ ID NO: 27) | 5'-AAC CTC ACC CAC GAT ATC ATC AC-3' |
| E266N-R (SEQ ID NO: 28) | 5'-ATT TTC CAG GTG CTG TAG TTT CCC-3' |
| K343N-F (SEQ ID NO: 29) | 5'-AAC GGG ACT GAA GCT G-3' |
| K343N-R (SEQ ID NO: 30) | 5'-CTC GTC GAT GGT CAG C-3' |

1-4. Construction of Alpha-1 Antitrypsin (Subtype M2) Vector (pT006)

To construct an alpha-1 antitrypsin vector, an alpha-1 antitrypsin vector (pT006) was constructed by cloning an alpha-1 antitrypsin gene into a pAV1 vector, using pEAT8 (encoding a1-AT (M2) cDNA) as a template. In detailed description, the pEAT8 (encoding a1-AT(M2) cDNA) template was amplified by PCR using two primers: XhoAT forward primer (5'-CCC TCC TCG AGA ATG CCG TCT TCT GTC TCG-3', SEQ ID NO: 1) and ATNot reverse primer (5'-GGG CCC GCG GCC GCA GTT ATT TTT GGG TGG G-3', SEQ ID NO: 2). Both ends of the amplified nucleotide were digested with two restriction enzymes XhoI and NotI, and fused with an expression vector pAV1 having an XhoI/NotI restriction site, resulting in the construction of an alpha-1 antitrypsin vector (pT006, SEQ ID NO: 40).

1-5. Preparation of Alpha-1 Antitrypsin (M2) Variant

To prepare an alpha-1 antitrypsin (M2) variant having a glycosylation site added thereto, the alpha-1 antitrypsin vector (pT006) prepared in Example 1-4 was used as a template. Pair of two primers (i.e., a forward primer (SEQ ID NO: 5) and a reverse primer (SEQ ID NO: 6)) and a mutagenesis kit (Enzynomix, EZchange™ Site-Directed Mutagenesis Kit) were used to prepare an alpha-1 antitrypsin (M2) variant vector (AT9N (M2)). The amino acid sequence of the resulting alpha-1 antitrypsin variant was set forth in SEQ ID NO: 42.

1-6. Preparation of Dimers of Alpha-1 Antitrypsins and Variants Thereof

To prepare an alpha-1 antitrypsin variant dimer, the pAT9N (subtype M2) was used as the alpha-1 antitrypsin variant. To construct a dimer vector, the pAT9N (M2) used as the template was amplified by PCR using two primers: XhoAT forward primer 2 (5'-GGG CCC CTC GAG GCC ACC ATG CCG TCT TCT GTC TCG TGG GGC ATC CTC CTG CTG GCA GGC CTG TGC TGC CTG GTC CCT GTC TCC CTG GCT GAA GAT CCC CAG GGA-3', SEQ ID NO: 31) and ATBam reverse primer 2 (5'-GGG GGG ATC CTC TTT TTG GGT GGG ATT CAC-3', SEQ ID NO: 32). Both ends of the amplified nucleotide were digested with two restriction enzymes XhoI and BamHI, and fused with an expression vector pAT9N (M2) having an XhoI/BamHI restriction site, resulting in the construction of an alpha-1 antitrypsin dimer vector (pAT9N (M2)-AT9N (M2)).

1-7. Expression of Dimers of Alpha-1 Antitrypsins and Variants Thereof

Chinese hamster ovary cells (CHO-K1) were used to express the proteins of the alpha-1 antitrypsin (T003, T006) and variants thereof and the dimer prepared in Examples 1-2,3,4,5 and 6. The CHO-K1 was incubated in a Dulbecco's Modified Eagle Medium (DMEM) supplemented with 10% fetal bovine serum (FBS) and an antibiotic under conditions of 5% $CO_2$ and 37° C. A day before introducing the expression vectors containing the alpha-1 antitrypsin and variant thereof, cells were seeded at a density of $5 \times 10^6$ cells in a 100 mm culture dish, and cultured. Thereafter, 800 µL of DMEM devoid of FBS and an antibiotic and 10 µg of each of the expression vectors containing alpha-1 antitrypsin and a variant thereof and the dimer were mixed, and kept at room temperature for one minute. The resulting mixture was then mixed with 20 µg of polyethylenimine (PEI, linear, Polysciences Inc. (Cat. no: 23966, MW: about 25,000)), and kept at room temperature for approximately 10 to 15 minutes. In this case, the cells cultured a day before were washed with PBS, and 6 mL of a fresh DMEM culture broth was added. After 10 to 15 minutes, each of the expression vectors containing the alpha-1 antitrypsin and variant thereof and the dimer kept at room temperature was added to the culture dish. The next day, the cells were washed with PBS, and put into an Iscove's Modified Dulbecco's Medium (IMDM, Cat. No 12200-028, Gibco) devoid of FBS and the protein expression was confirmed.

1-8. Purification of Alpha-1 Antitrypsin and Variant Thereof and Dimer

The alpha-1 antitrypsin and variant thereof and the dimer expressed in Example 1-7 were purified as follows. More particularly, to purify the alpha-1 antitrypsin and variant thereof and the dimer secreted in a cell culture broth, the culture broth was centrifuged to remove cells, and only a cell supernatant was recovered, and diluted with an equilibrium buffer (20 mM sodium phosphate, pH 8.0). Thereafter, the cell supernatant diluted with the equilibrium buffer was put into a Q-Sepharose (GE Healthcare, US) column equilibrated with an equilibrium buffer, and thoroughly washed with an equilibrium buffer. Then, a protein was eluted at an increasing concentration (0 to 400 mM NaCl, 20 mM sodium phosphate, pH 8.0) of sodium chloride. The eluted protein was put into an Alpha-1 Antitrypsin Select (GE Healthcare, US) column equilibrated with an equilibrium buffer (50 mM Tris, 0.15 M sodium chloride, pH 7.5), and then thoroughly washed with an equilibrium buffer. Then, the protein was eluted at an increasing concentration of $MgCl_2$. The resulting solution was dialyzed in phosphate buffered saline, and then concentrated using Vivaspin20 (GE Healthcare, US) to obtain the purified protein with high purity. The SDS-PAGE results of the purified alpha-1 antitrypsin and variant thereof and the dimer are shown in FIG. 3.

As shown in FIG. 3, it was confirmed that the alpha-1 antitrypsin variants having the N-glycosylation site added thereto were observed at a relatively higher position than the wild-type alpha-1 antitrypsin (T003 or T006), which indicated that the molecular weight of the alpha-1 antitrypsin variant was increased by glycosylation. Also, it was revealed that the dimer was observed at a position corresponding to the molecular weight of the dimer, and there was a slight difference in molecular weight position according to a level of glycosylation.

EXAMPLE 2

Preparation of Fusion Protein of Human Growth Hormone/Alpha-1 Antitrypsin Variant To prepare a fusion protein of a human growth hormone/alpha-1 antitrypsin variant (AT9N), the pAT9N (subtype M2) was used as the alpha-1 antitrypsin variant. To construct a fusion vector, a human growth hormone gene (IOH45734, Invitrogen) used as a template was amplified by PCR using two primers: XhoGH forward primer (5'-GGG CCC CTC GAG GCC ACC ATG GCT ACA GGC TCC CGG-3', SEQ ID NO: 33) and GHBam reverse primer (5'-GGG GGG ATC CTC GAA GCC ACA GCT GCC CTC-3', SEQ ID NO: 34). Both ends of the amplified nucleotide were digested with two restriction enzymes XhoI and BamHI, and then fused with an expression vector pAT9N (M2) having an XhoI/BamHI restriction site, resulting in the construction of a human growth hormone/alpha-1 antitrypsin variant fusion vector (phGH-AT9N (M2), SEQ ID NO: 43).

EXAMPLE 3

Preparation of Fusion Protein of Granulocyte Colony Stimulating Factor/Alpha-1 Antitrypsin Double Variant 3-1. Preparation of Alpha-1 Antitrypsin Double Variant The alpha-1 antitrypsin variant (AT9N) vector constructed in the same manner as in Example 1-5 was used as the template, and the following two primers: forward primer (5'-CCA TGT TTT TAG AGG CCA TAA ACA TGT CTA TCC CCC CC-3', SEQ ID NO: 35) and reverse primer (5'-GGG GGG GAT AGA CAT GTT TAT GGC CTC TAA AAA CAT GG-3', SEQ ID NO: 36), and a mutagenesis kit (Enzynomix, EZchange™ Site-Directed Mutagenesis Kit) were used to construct a vector pT004N (Q9N, P357N) containing an alpha-1 antitrypsin double variant in which glutamine at a $9^{th}$ position of the N-terminus of alpha-1 antitrypsin was substituted with asparagine and proline at a $357^{th}$ position was also substituted with asparagine. The amino acid sequence of the resulting alpha-1 antitrypsin double variant was set forth in SEQ ID NO: 44.

3-2. Preparation of Fusion Protein of Granulocyte Colony Stimulating Factor/Alpha-1 Antitrypsin Double Variant To prepare a fusion protein of granulocyte colony stimulating factor/alpha-1 antitrypsin double variant, the pT004N (Q9N, P357N) containing the alpha-1 antitrypsin double variant prepared by the method in Example 3-1 was used. To construct a fusion vector, a granulocyte colony stimulating factor (IHS1380-97652343, Open Biosystems) used as the template was amplified by PCR using two primers: XhoCSF forward primer (5'-GGG CCC CTC GAG ATG GCT GGA CCT GCC ACC-3', SEQ ID NO: 37) and CSFBam reverse primer (5'-GGG GGG ATC CTC GGG CTG GGC AAG GTG GCG-3', SEQ ID NO: 38). Both ends of the amplified nucleotide were digested with two restriction enzymes XhoI and BamHI, and fused with an expression vector pT004N having an XhoI/BamHI restriction site, resulting in the construction of a granulocyte colony stimulating factor/alpha-1 antitrypsin double variant fusion vector (pT603N, SEQ ID NO: 45). Subsequently, the fusion protein of granulocyte colony stimulating factor/alpha-1 antitrypsin double variant was expressed and purified from the resulting fusion vector (pT603N) in the same manner as in Examples 1-7 and 1-8.

EXPERIMENTAL EXAMPLE 1

Pharmacokinetics of Plasma-Derived Alpha-1 Antitrypsin, Alpha-1 Antitrypsin Prepared in Chinese Hamster Ovary Cells, and Variants Thereof To determine the pharmacokinetics of the plasma-derived alpha-1 antitrypsin and the alpha-1 antitrypsin prepared in Chinese hamster ovary cells according to the present invention, experiments were carried out as follows.

Male Sprague-Dawley rats were used as laboratory animals, and allotted into several experimental groups (N=3 to 5). A plasma-derived human alpha-1 antitrypsin (Calbiochem, US), a recombinant alpha-1 antitrypsin and variants thereof were subcutaneously or intravenously injected to the Sprague-Dawley rats in each group at a dose of 445 μg per rat, and phosphate buffered saline was used as a diluted solution. Blood was drawn after each administration, and then centrifuged to obtain sera. The sera from each administration were stored in a freezer until analysis was carried out, and the blood concentrations of the alpha-1 antitrypsin and variant thereof were measured using an enzyme-linked immunosorbent assay (ELISA). The ELISA was performed using two methods. One method was performed as follows. A plate (Nunc, Denmark) was coated with a monoclonal antibody (Medix Biochemica, Finland) against the human alpha-1 antitrypsin, and treated with phosphate buffered saline in which 1% bovine serum albumin was dissolved. A sample was diluted with phosphate buffered saline in which 1% bovine serum albumin was dissolved, and used. An anti-alpha-1 antitrypsin monoclonal antibody-biotin conjugate fused using sulfo-NHS-biotin (Pierce biotechnology, US), and streptavidin-HRP were used to detect the alpha-1 antitrypsin. A colorimetric reaction was performed using 3,3',5,5'-tetramethylbenzidine (TMB) and a hydrogen peroxide colorimetric solution. Then, sulfuric acid was added to each well to stop the reaction, and the reaction solution was measured for absorbance at 450 nm using a microplate reader (Molecular Device, US). The other method was performed as follows. A plate (Nunc, Denmark) was coated with a monoclonal antibody (Medix Biochemica, Finland) against the human alpha-1 antitrypsin, and treated with phosphate buffered saline in which 1% bovine serum albumin was dissolved. A sample was diluted with phosphate buffered saline in which 1% bovine serum albumin was dissolved, and used. An anti-alpha-1 antitrypsin polyclonal antibody-biotin conjugate (Abcam, United Kingdom) and streptavidin-HRP were used to detect the alpha-1 antitrypsin. A colorimetric reaction was performed using 3,3',5,5'-tetramethylbenzidine (TMB) and a hydrogen peroxide colorimetric solution. Then, sulfuric acid was added to each well to stop the reaction, and the reaction solution was measured for absorbance at 450 nm using a microplate reader (Molecular Device, US). The plate was washed with a washing solution (0.05% Tween 20, phosphate buffered saline) in each step. A quantitative value of each sample was calculated through regression analysis after a standard curve was plotted for a standard reference material.

The pharmacokinetic graphs plotted for the plasma-derived alpha-1 antitrypsin, the alpha-1 antitrypsin derived from Chinese hamster ovary cells, and variants thereof upon subcutaneous administration and intravenous administration are shown in FIGS. 4 to 7.

Figure 4:
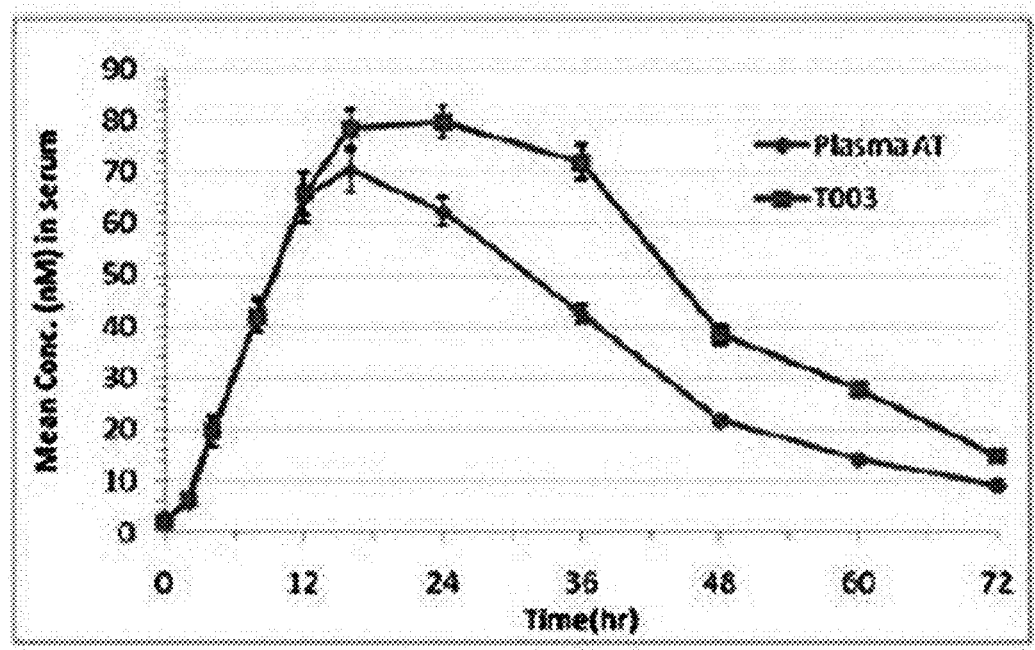
FIG. 4 is a pharmacokinetic graph plotted for a plasma-derived alpha-1 antitrypsin and a recombinant alpha-1 antitrypsin expressed in animal cells upon subcutaneous administration according to the present invention.
Figure 5:
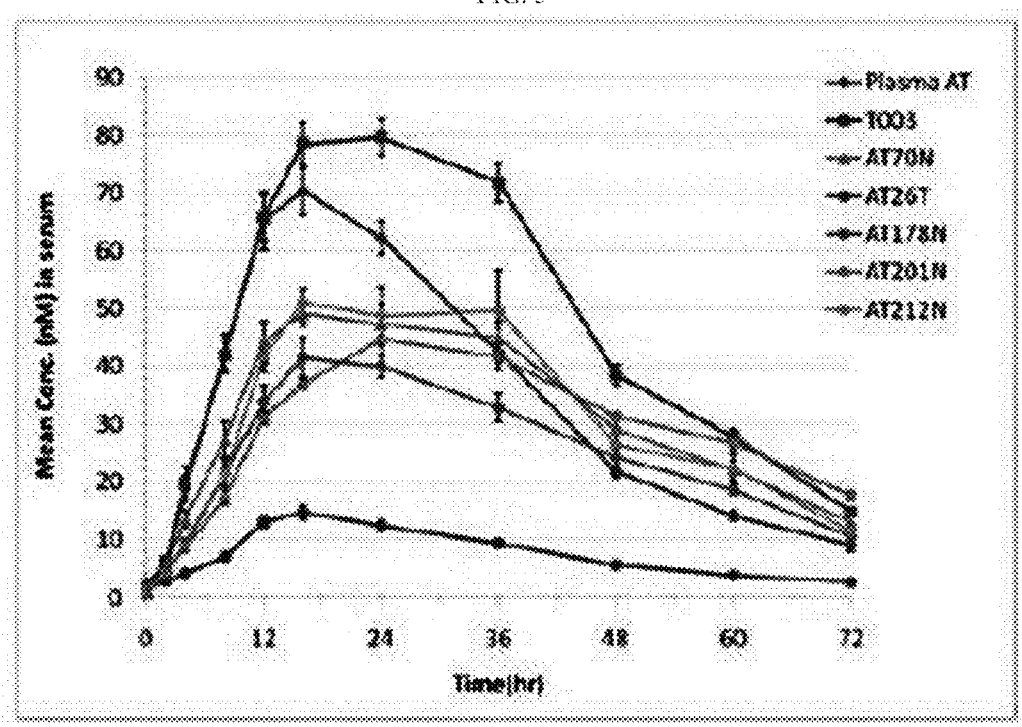
FIG. 5 is a pharmacokinetic graph plotted for alpha-1 antitrypsin and variants thereof upon subcutaneous administration according to the present invention.

As shown in FIGS. 4 and 5, the pharmacokinetics of the plasma-derived alpha-1 antitrypsin, the recombinant alpha-1 antitrypsin and the variants thereof upon subcutaneous administration were observed in various aspects. As shown in FIG. 4, it was revealed that the plasma-derived alpha-1 antitrypsin had a half-life ($t_{1/2}$) in the body of approximately 15.2 hours, $T_{max}$ of 16.8 hours, and an AUC (hr*μg/mL) value of 113.1, and the recombinant alpha-1 antitrypsin (T003) had a half-life ($t_{1/2}$) in the body of approximately 16.5 hours, $T_{max}$ of 20.8 hours, and an AUC (hr*μg/mL) value of 156.6 hours. Therefore, the alpha-1 antitrypsin prepared in the Chinese hamster ovary cells showed similar pharmacokinetic profiles to those of the plasma-derived alpha-1 antitrypsin. The half-life ($t_{1/2}$) and $T_{max}$ of the recombinant alpha-1 antitrypsin were slightly increased, and the AUC (hr*μg/mL) was also increased by approximately 40%, compared to those of the plasma-derived alpha-1 antitrypsin. Also, it was revealed that the alpha-1 antitrypsin isoforms M2 type (His101) and M3 type (Arg101) showed similar profiles within a range of experimental error in the pharmacokinetics test using animals.

On the other hand, the pharmacokinetics of the alpha-1 antitrypsin variants prepared in the Chinese hamster ovary cells showed different profiles depending on the glycosylation sites to be added.

As shown in FIG. 5, it was revealed that the AUCINF_obs (hr*μg/mL) of AT70N, AT178N, AT201N, and AT212N were lower with approximately 50 to 70% than that of the alpha-1 antitrypsin (T003) prepared in the Chinese hamster ovary cells. However, it was revealed that the half-lives of the variants in the body were increased by approximately 15 to 90%, compared to that of the wild-type alpha-1 antitrypsin prepared in the Chinese hamster ovary cells, demonstrating that the addition of the glycosylation site was considered to have an influence on the half-lives in the body. On the other hand, the AUC (hr*μg/mL) of the AT148T was similar to that of the alpha-1 antitrypsin prepared in the Chinese hamster ovary cells, but the in vivo half-life was 24.6 hours, which was increased by approximately 50%, compared to that of recombinant alpha-1 antitrypsin. This indicated that the pharmacokinetics of the AT148T was improved due to addition of the glycosylation site.

As shown in FIG. 5, it was revealed that the in vivo half-life of AT26T was slightly increased, compared to that of alpha-1 antitrypsin (T003) prepared in the Chinese hamster ovary cells, but AUC (hr*μg/mL) of AT26T was merely approximately 17% of the alpha-1 antitrypsin (T003) prepared in the Chinese hamster ovary cells, and the in vivo clearance rate (CL/F; mL/hr/kg) of AT26T was also approximately 6 times higher than that of the alpha-1 antitrypsin (T003), indicating that addition of the glycosylation site at the $26^{th}$ position had the worst influence on the pharmacokinetics.

Figure 6:
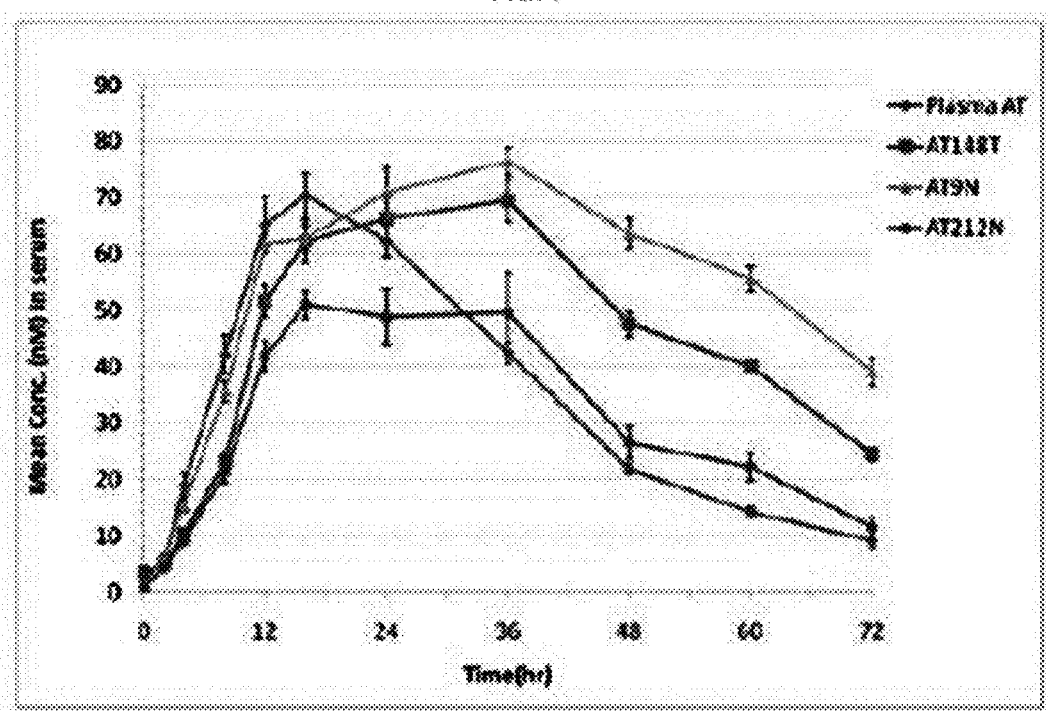
FIG. 6 is a pharmacokinetic graph plotted for plasma-derived alpha-1 antitrypsin and recombinant alpha-1 antitrypsin variants upon subcutaneous administration according to the present invention.

FIG. 6 is a pharmacokinetic graph plotted for the plasma-derived alpha-1 antitrypsin and the recombinant alpha-1 antitrypsin variants upon subcutaneous administration. As shown in FIG. 6, it was revealed that the plasma-derived alpha-1 antitrypsin had a in vivo half-life ($t_{1/2}$) of approximately 15.2 hours, and, among the alpha-1 antitrypsin variants, AT148T had an in vivo half-life of 24.6 hours, AT9N had an in vivo half-life of 37.7 hours, and AT212N had an in vivo half-life of 19.1 hours, indicating that the pharmacokinetics of the alpha-1 antitrypsin variants showed various profiles depending on the additional glycosylation sites.

From the aforementioned results, it was confirmed that the half-lives of the alpha-1 antitrypsin variants (AT26T, AT148T, AT178N, AT201N, and AT212N) which were further glycosylated by mutating a loop region of alpha-1 antitrypsin were slightly increased, compared to the recombinant alpha-1 antitrypsin which was not further glycosylated, but the other pharmacokinetic profiles were much inferior to the wild-type recombinant alpha-1 antitrypsin (T003). Accordingly, it could be concluded that these glycosylated variants at loop region were clinically not superior to the wild-type alpha-1 antitrypsin.

However, it could be concluded that, among the variants obtained by additional glycosylation of the recombinant alpha-1 antitrypsin, the variant in which the glycosylation site was added at the $9^{th}$ position of the N-terminus had remarkably improved sustainability in the body, compared to the variants in which the glycosylation site was added at the other positions, and had a remarkably low clearance rate from the body. Therefore, the changes in pharmacokinetic parameters were confirmed by addition of glycosylation at a position downstream from a $25^{th}$ amino acid residue in the N-terminal peptide structure of the alpha-1 antitrypsin.

FIG. 7 shows the pharmacokinetic test results on the variants which were obtained by adding glycosylation sites at $4^{th}$, $9^{th}$ and $12^{th}$ positions of the N-terminus of alpha-1 antitrypsin. As shown in FIG. 7, it was shown that when the glycosylation sites were added at $9^{th}$ or $12^{th}$ positions, the variant had an excellent in vivo half-life or Area Under the Curve (AUC), compared to the variant in which the glycosylation site was added at a $4^{th}$ position. The N-terminal region of the alpha-1 antitrypsin was not observed in the X-ray crystal structure, thus having an amorphous structure in a solution, and moving freely. When the N-terminal region was glycosylated, it could be inferred that the increase in the hydrodynamic volume caused the increase of in vivo half-life of alpha-1 antitrypsin, and also these variants had increased bioavailability in the body after injection.

EXPERIMENTAL EXAMPLE 2

Pharmacokinetics of Plasma-Derived Alpha-1 Antitrypsin, Alpha-1 Antitrypsin Prepared in Chinese Hamster Ovary Cells, and Dimers Thereof To determine the pharmacokinetics of the alpha-1 antitrypsin dimer prepared in the Chinese hamster ovary cells according to the present invention, experiments were performed as follows. Sequences coding for proteins in which a glycosylation site was added at a $9^{th}$ position of alpha-1 antitrypsin were linked in parallel, and cloned. Thereafter, the dimer AT9N (M2)-AT9N (M2) and the monomer T003 expressed in CHO cells were purified, and subjected to a pharmacokinetics test.

Figure 8:
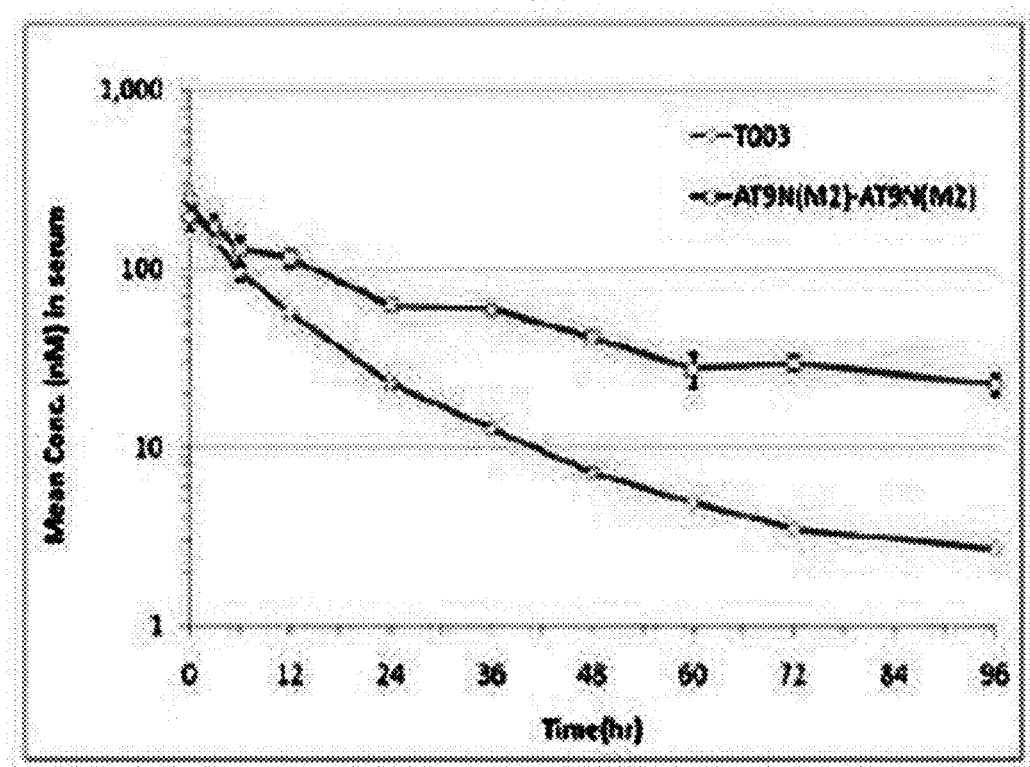
FIG. 8 is a pharmacokinetic graph plotted for alpha-1 antitrypsin and a dimer thereof upon intravenous administration according to the present invention.

As shown in FIG. 8, it was shown that the in vivo half-life of AT9N (M2)-AT9N (M2) dimer was 32.8 hours, which was twice the in vivo half-life (16.5 hours) of the T003, and the AUC value of the AT9N (M2)-AT9N (M2) dimer also increased twofold. It was also revealed that a clearance value of the AT9N (M2)-AT9N (M2) dimer was remarkably reduced. From these results, it was confirmed that the alpha-1 antitrypsin variant monomer as well as alpha-1 antitrypsin variant dimer having the increased in vivo stability were able to be used as a drug.

EXPERIMENTAL EXAMPLE 3

Inhibitory Effect of Alpha-1 Antitrypsin and Variants Thereof on Elastase Activities To determine an inhibitory effect of the alpha-1 antitrypsin and variants thereof according to the present invention on elastase activities, experiments were performed as follows.

Porcine pancreatic elastase (Calbiochem, Cat. 324682) and AAA-pNA (N-Succinyl-Ala-Ala-Ala-p-nitroanilide, Sigma, S4760) were used as an enzyme and a substrate, respectively, to measure the rate constants of the alpha-1 antitrypsin and variants thereof. More particularly, the porcine pancreatic elastase and the alpha-1 antitrypsin and variants thereof were mixed at the same molar ratio, and reacted at 25° C. for 120 seconds, 300 seconds, and 600 seconds. Thereafter, the AAA-pNA was added to the resulting reaction mixture, and measured for kinetics for 5 minutes at intervals of one minute. In the final reaction, the concentrations of the porcine pancreatic elastase and the alpha-1 antitrypsin and variants thereof were 20 nM, and the concentration of the AAA-pNA was 1 mM.

Because the reaction of the porcine pancreatic elastase with the alpha-1 antitrypsin and variants thereof was an irreversible secondary reaction (Levenspiel O. Chemical reaction engineering, 2nd edition. 1972, Wiley, New York), the rate constant was calculated by the equation: $1/R = kaC_{E0}t+1$ [R=Remaining PPE activity, ka=Rate constant ($M^{-1} s^{-1}$), $C_{E0}$=Initial concentration of AAT (M), and t=Reaction time (seconds)]. The association rate constant (ka) was calculated using the activities of porcine pancreatic elastase remaining at each reaction time. The results are listed in Table 2.

Also, the equilibrium constant of the alpha-1 antitrypsin and variants thereof was calculated using the following equation. The results are listed in Table 3.

$$Ka(M^{-1}) = [EI]/[E]f/[I]f \times 10^9$$

[E]T=Initial Concentration of Enzyme
[I]T=Initial Concentration of Inhibitor
$[E]f = [E]T \times (A_{test}/A_{control})$
$[EI] = [E]T - [E]f = [E]T \times (1 - A_{test}/A_{control})$
$[I]f = [I]T - [EI]$
A=Slope of t (Measurement Time) vs. Absorbance

TABLE 2

| Elastase inhibitor | Association rate constant (ka ($m^{-1}s^{-1}$)) |
| --- | --- |
| Plasma alpha-1 antitrypsin | $5.4 \times 10^5$ |
| T003 | $6.5 \times 10^5$ |
| AT9N | $6.0 \times 10^5$ |

TABLE 3

| Elastase inhibitor | Equilibrium constant (ka($M^{-1}$)) |
| --- | --- |
| Plasma alpha-1 antitrypsin | $2.60 \times 10^9$ |
| T003 | $3.56 \times 10^9$ |
| AT9N | $3.04 \times 10^9$ |

As listed in Tables 2 and 3, it was observed that the association rate constants and the equilibrium constants of the wild-type human alpha-1 antitrypsin (T003) and the alpha-1 antitrypsin variant AT9N were substantially similar to those of the plasma-derived human alpha-1 antitrypsin. Therefore, it was confirmed that the N-terminal glycosylation of the alpha-1 antitrypsin did not have an influence on the elastase inhibitor activities of alpha-1 antitrypsin. However, when the inhibitory effects of the AT148T and the plasma-derived alpha-1 antitrypsin against elastase were compared, AT148T had a binding affinity of half that of the wild-type alpha-1 antitrypsin. Therefore, it could be seen that even if AT148T had an influence on the half-life in the body due to addition of the glycosylation, but the glycosylation at the $148^{th}$ position of alpha-1 antitrypsin had a negative effect on binding of alpha-1 antitrypsin to a proteolytic enzyme (i.e., protease).

The variants such as AT70N and AT178N had remarkably reduced binding affinity with elastase, compared to the wild-type plasma-derived alpha-1 antitrypsin. From these facts, it could be concluded that when a glycosylation site was added at a specific position of alpha-1 antitrypsin, it was very important to select a glycosylation position(s) which did not affect the alpha-1 antitrypsin activities although the glycosylation was able to affect the pharmacokinetics in the body.

EXPERIMENTAL EXAMPLE 4

Pharmacokinetic Test on Human Growth Hormone/Alpha-1 Antitrypsin Variant Fusion

To determine the pharmacokinetics of the fusion protein of the human growth hormone/alpha-1 antitrypsin variant according to the present invention, experiments were performed as follows. Sprague-Dawley rats were used as laboratory animals, and allotted into a human growth hormone-administered group (N=3) and a fusion-administered group (N=5). The human growth hormone/alpha-1 antitrypsin fusion protein prepared in Example 2 was subcutaneously injected into the Sprague-Dawley rats at a dose of 720 µg per rat, and phosphate buffered saline was used as a diluted solution. After the time points of 0, 1, 2, 4, 8, 12, 16, 24, 30, and 48 hours, blood was drawn, and then centrifuged to obtain sera. A human growth hormone, Scitropin (SciGen, Singapore), was subcutaneously injected as the control at a dose of 200 µg per rat, and phosphate buffered saline was used as the diluted solution. After the time points of 0, 0.33, 1, 2, 5, 8, 12, 18, 24, 30, and 48 hours, blood was drawn, and then centrifuged to obtain sera. Each sample was analyzed using an ELISA as will be described below. A monoclonal antibody (Medix Biochemica, Finland) against a human growth hormone was diluted with phosphate buffered saline at a concentration of 1 to 5 µg/mL, and divided into each well of a 96-well plate (Nunc, Denmark) at an amount of 100 µL. Thereafter, the resulting solution was kept at room temperature for 15 to 18 hours. The antibody which was not attached to the well plate was removed, and phosphate buffered saline in which 1% bovine serum albumin was dissolved was divided at an amount of 250 µL, kept at room temperature for 2 hours, and then washed 3 times with a washing solution (0.05% Tween 20, phosphate buffered saline) to remove the solution. A sample was diluted with phosphate buffered saline in which 1% bovine serum albumin was dissolved, added to the 96-well plate, and reacted at room temperature for 2 hours. The 96-well plate was washed 5 times with a washing solution, and an anti-human growth hormone monoclonal antibody-biotin conjugate conjugated using sulfo-NHS-biotin (Pierce biotechnology, US) was diluted with a diluent solution, and divided into each well of the 96-well plate at an amount of 100 µL. Subsequently, the 96-well plate was reacted at room temperature for 2 hours, and washed 5 times with a washing solution. Then, a streptavidin-HRP solution was added to the 96-well plate, and reacted at room temperature for 30 minutes. The 96-well plate was washed 5 times with a washing solution, and 100 µL of a colorimetric solution of 3,3',5,5'-tetramethylbenzidine (TMB) and hydrogen peroxide was put into each well, and reacted for 30 minutes in a dark place. 100 μL of 1M sulfuric acid was added to each well to stop the reaction, and measured for absorbance at 450 nm using a VersaMax microplate reader (Molecular Device, US). A quantitative value of each sample was calculated through regression analysis after a standard curve was plotted for a standard reference material.

Figure 9:
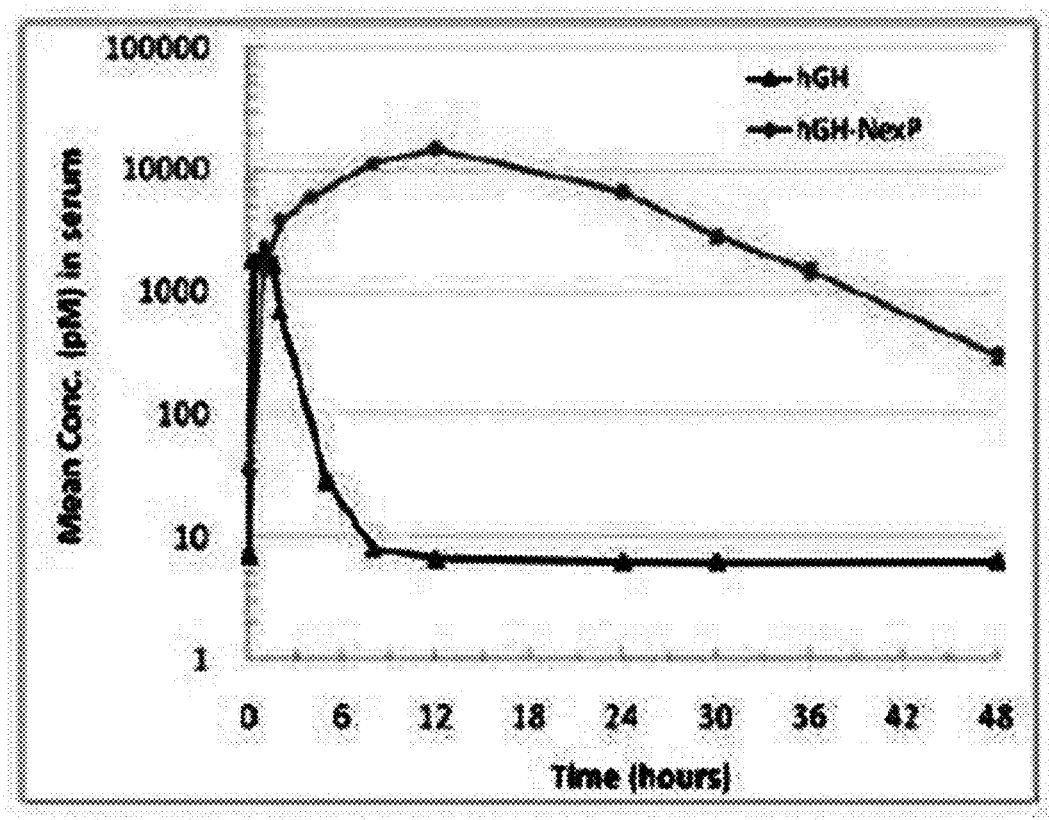
FIG. 9 is a pharmacokinetic graph plotted for a human growth hormone/alpha-1 antitrypsin variant fusion upon subcutaneous administration according to the present invention.

The pharmacokinetic graph of the human growth hormone/alpha-1 antitrypsin variant fusion protein according to the present invention is shown in FIG. 9.

As shown in FIG. 9, it could be seen that the blood half-life ($t_{1/2}$) of the human growth hormone/alpha-1 antitrypsin variant fusion protein according to the present invention was approximately 6 hours, which was more than 4 times that of the human growth hormone, indicating that the variant fusion protein had remarkably increased stability in the body.

EXPERIMENTAL EXAMPLE 5

Pharmacokinetic Test on Granulocyte Colony Stimulating Factor/Alpha-1 Antitrypsin Double Variant Fusion To determine the pharmacokinetic of the fusion protein of the granulocyte colony stimulating factor/alpha-1 antitrypsin double variant according to the present invention, experiments were performed as follows. Sprague-Dawley rats were used as laboratory animals, and allotted into a granulocyte colony stimulating factor-administered group (N=5) and a fusion protein-administered group (N=3). The granulocyte colony stimulating factor/alpha-1 antitrypsin double variant fusion protein (pT603N) prepared in Example 3 was subcutaneously injected to the Sprague-Dawley rats at a dose of 340 μg per rat, and phosphate buffered saline (PBS) was used as a diluted solution. After the time points of 0, 1, 2, 4, 8, 12, 16, 24, 36, 48, 60, and 72 hours after subcutaneous injection, blood was drawn, and then centrifuged to obtain sera. A granulocyte colony stimulating factor, Grasin (Filgrastim), was diluted with phosphate buffered saline, and subcutaneously injected as the control at a dose of 100 μg per rat. After the time points of 0, 0.5, 1, 2, 4, 8, 12, 16, 24, 36, and 48 hours, blood was drawn, and then centrifuged to obtain sera. Each sample was analyzed using an ELISA as will be described below. A monoclonal antibody (R&D Systems) against the granulocyte colony stimulating factor was diluted with phosphate buffered saline at a concentration of 1 to 10 μg/mL, and divided into each well of a 96-well plate (Nunc, Denmark) at an amount of 100 μL. Thereafter, the resulting solution was kept at room temperature for 15 to 18 hours. The antibody which was not attached to the well plate was then removed, and phosphate buffered saline in which 1% bovine serum albumin was dissolved was divided at an amount of 250 μL, kept at room temperature for 2 hours, and then washed 3 times with a washing solution (0.05% Tween 20, phosphate buffered saline) to remove the solution. A sample was diluted with phosphate buffered saline in which 1% bovine serum albumin was dissolved, added to the 96-well plate, and reacted at room temperature for 2 hours. The 96-well plate was washed 5 times with a washing solution, and an anti-granulocyte colony stimulating factor polyclonal antibody-biotin conjugate (R&D Systems) was diluted with a diluent solution, and divided into each well of the 96-well plate at an amount of 100 μL. Subsequently, the 96-well plate was reacted at room temperature for 2 hours, and washed 5 times with a washing solution. Then, a streptavidin-HRP solution was added to the 96-well plate, and reacted at room temperature for 30 minutes. The 96-well plate was washed 5 times with a washing solution, and 100 μL of a colorimetric solution of 3,3',5,5'-tetramethylbenzidine (TMB) and hydrogen peroxide was put into each well, and reacted for 30 minutes in a dark place. 100 μL of 1M sulfuric acid was added to each well to stop the reaction, and measured for absorbance at 450 nm using a VersaMax microplate reader (Molecular Device, US). A quantitative value of each sample was calculated through regression analysis after a standard curve was plotted for a standard reference material. The pharmacokinetic graph of the granulocyte colony stimulating factor/alpha-1 antitrypsin variant fusion protein according to the present invention is shown in FIG. 10.

As shown in FIG. 10, it was confirmed that the granulocyte colony stimulating factor/alpha-1 antitrypsin double variant fusion protein according to the present invention showed blood half-life ($t_{1/2}$) of approximately 7.3 hours, which was approximately 3 times more than the blood half-life (2.7 hours) of the granulocyte colony stimulating factor, and the AUC was remarkably increased to 3 times or more than that of the granulocyte colony stimulating factor. From the results, it was concluded that when a heterogeneous protein such as a physiologically active protein was linked to the alpha-1 antitrypsin double variant, the half-life of the heterogeneous protein was increased.

Industrial Applicability

When the alpha-1 antitrypsin variant having an N-glycosylation site added thereto through amino acid mutation between $1^{st}$ and $25^{th}$ positions of the N-terminus according to the present invention is used to prevent or treat alpha-1 antitrypsin deficiency, the blood half-life ($t_{1/2}$) and the area under blood drug concentration vs. time curve (AUC) can be remarkably increased to exhibit excellent stability in the body and maintain an inhibitory effect on elastase activities. Therefore, the alpha-1 antitrypsin variant according to the present invention can be used to treat alpha-1 antitrypsin deficiency, and can be useful in increasing the half-life of a heterogeneous protein in the body when the heterogeneous protein is linked to the alpha-1 antitrypsin variant. Accordingly, the alpha-1 antitrypsin variant according to the present invention can be useful in preventing or treating alpha-1 antitrypsin deficiency.

The present invention has been described in detail. However, it should be understood that the detailed description and specific examples, while indicating preferred embodiments of the invention, are given by way of illustration only, and various changes and modifications within the spirit and scope of the invention will become apparent to those skilled in the art from this detailed description.

The invention claimed is:

1. An alpha-1 antitrypsin variant prepared by substituting an amino acid at a specific site between $1^{st}$ and $25^{th}$ positions of the N-terminus of alpha-1 antitrypsin in order to add a glycosylation site, wherein the specific site is at the $9^{th}$ or $12^{th}$ position.

2. A method of preparing the alpha-1 antitrypsin variant of claim 1, comprising:

a) substituting an amino acid at a specific site at the $9^{th}$ or $12^{th}$ position of the N-terminus of alpha-1 antitrypsin in order to add a glycosylation site;

b) culturing cells transformed with an alpha-1 antitrypsin expression vector having the glycosylation site added thereto in a culture medium;

c) expressing an alpha-1 antitrypsin variant protein from the cells; and d) purifying and recovering the expressed alpha-1 antitrypsin variant protein.

3. A composition for treating alpha-1 antitrypsin deficiency, comprising the alpha-1 antitrypsin variant of claim 1 as an active ingredient, and the alpha-1 antitrypsin deficiency is a chronic obstructive pulmonary disease.

4. A method of treating alpha-1 antitrypsin deficiency, comprising:

administering a therapeutically effective amount of the alpha-1 antitrypsin variant of claim 1 to a patient in need thereof, and the alpha-1 antitrypsin deficiency is a chronic obstructive pulmonary disease.

5. An alpha-1 antitrypsin variant fusion having an increased half-life in the body relative to a naturally occurring alpha-1 antitrypsin protein, wherein the fusion is prepared by linking two alpha-1 antitrypsin variants of claim 1.

6. An alpha-1 antitrypsin variant fusion comprising a heterogeneous protein having an increased half-life in the body relative to a naturally occurring alpha-1 antitrypsin protein, wherein the fusion is prepared by linking the alpha-1 antitrypsin variant of claim 1 to the heterogeneous protein.

7. The alpha-1 antitrypsin variant fusion of claim 6, wherein the alpha-1 antitrypsin variant having an amino acid proline at the $357^{th}$ position, which is a P2 position, and is further substituted with asparagine.

* * * * *

SEQUENCE LISTING

<160> NUMBER OF SEQ ID NOS: 45

<210> SEQ ID NO 1
<211> LENGTH: 30
<212> TYPE: DNA

```
<213> ORGANISM: Artificial Sequence
<220> FEATURE:
<223> OTHER INFORMATION: A1AT forward primer 1

<400> SEQUENCE: 1
ccctcctcga gaatgccgtc ttctgtctcg                                    30

<210> SEQ ID NO 2
<211> LENGTH: 31
<212> TYPE: DNA
<213> ORGANISM: Artificial Sequence
<220> FEATURE:
<223> OTHER INFORMATION: A1AT reverse primer 1

<400> SEQUENCE: 2
gggcccgcgg ccgcagttat ttttgggtgg g                                  31

<210> SEQ ID NO 3
<211> LENGTH: 30
<212> TYPE: DNA
<213> ORGANISM: Artificial Sequence
<220> FEATURE:
<223> OTHER INFORMATION: Q4N forward primer

<400> SEQUENCE: 3
aacggaactg ctgcccagaa gacagataca                                    30

<210> SEQ ID NO 4
<211> LENGTH: 21
<212> TYPE: DNA
<213> ORGANISM: Artificial Sequence
<220> FEATURE:
<223> OTHER INFORMATION: Q4N reverse primer

<400> SEQUENCE: 4
gggatcctca gccagggaga c                                             21

<210> SEQ ID NO 5
<211> LENGTH: 21
<212> TYPE: DNA
<213> ORGANISM: Artificial Sequence
<220> FEATURE:
<223> OTHER INFORMATION: Q9N forward primer

<400> SEQUENCE: 5
aacaagacag atacatccca c                                             21

<210> SEQ ID NO 6
<211> LENGTH: 21
<212> TYPE: DNA
<213> ORGANISM: Artificial Sequence
<220> FEATURE:
<223> OTHER INFORMATION: Q9N reverse primer

<400> SEQUENCE: 6
ggcagcatct ccctggggat c                                             21

<210> SEQ ID NO 7
<211> LENGTH: 27
<212> TYPE: DNA
<213> ORGANISM: Artificial Sequence
<220> FEATURE:
<223> OTHER INFORMATION: D12N forward primer

<400> SEQUENCE: 7
aatacaaccc accatgatca ggatcac                                       27
```

```
<210> SEQ ID NO 8
<211> LENGTH: 21
<212> TYPE: DNA
<213> ORGANISM: Artificial Sequence
<220> FEATURE:
<223> OTHER INFORMATION: D12N reverse primer

<400> SEQUENCE: 8
tgtcttctgg gcagcatctc c                                              21

<210> SEQ ID NO 9
<211> LENGTH: 19
<212> TYPE: DNA
<213> ORGANISM: Artificial Sequence
<220> FEATURE:
<223> OTHER INFORMATION: I26T forward primer

<400> SEQUENCE: 9 actacccca acctggctg                                                  19

<210> SEQ ID NO 10
<211> LENGTH: 22
<212> TYPE: DNA
<213> ORGANISM: Artificial Sequence
<220> FEATURE:
<223> OTHER INFORMATION: I26T reverse primer

<400> SEQUENCE: 10
cttgttgaag gttgggtgat cc                                             22

<210> SEQ ID NO 11
<211> LENGTH: 24
<212> TYPE: DNA
<213> ORGANISM: Artificial Sequence
<220> FEATURE:
<223> OTHER INFORMATION: A31T forward primer

<400> SEQUENCE: 11
actgagttcg ccttcagcct atac                                           24

<210> SEQ ID NO 12
<211> LENGTH: 22
<212> TYPE: DNA
<213> ORGANISM: Artificial Sequence
<220> FEATURE:
<223> OTHER INFORMATION: A31T reverse primer

<400> SEQUENCE: 12
caggttgggg gtgatcttgt tg                                             22

<210> SEQ ID NO 13
<211> LENGTH: 20
<212> TYPE: DNA
<213> ORGANISM: Artificial Sequence
<220> FEATURE:
<223> OTHER INFORMATION: L66N forward primer

<400> SEQUENCE: 13
aacgggacca aggctgacac                                                20

<210> SEQ ID NO 14
<211> LENGTH: 22
<212> TYPE: DNA
<213> ORGANISM: Artificial Sequence
<220> FEATURE:
```

<223> OTHER INFORMATION: L66N reverse primer

<400> SEQUENCE: 14
ggagagcatt gcaaaggctg ta                                          22

<210> SEQ ID NO 15
<211> LENGTH: 24
<212> TYPE: DNA
<213> ORGANISM: Artificial Sequence
<220> FEATURE:
<223> OTHER INFORMATION: A70N forward primer

<400> SEQUENCE: 15
aacgacactc acgatgaaat cctg                                        24

<210> SEQ ID NO 16
<211> LENGTH: 18
<212> TYPE: DNA
<213> ORGANISM: Artificial Sequence
<220> FEATURE:
<223> OTHER INFORMATION: A70N reverse primer

<400> SEQUENCE: 16
cttggtcccc agggagag                                               18

<210> SEQ ID NO 17
<211> LENGTH: 21
<212> TYPE: DNA
<213> ORGANISM: Artificial Sequence
<220> FEATURE:
<223> OTHER INFORMATION: G148N forward primer

<400> SEQUENCE: 17
aacgacaccg aagaggccaa g                                           21

<210> SEQ ID NO 18
<211> LENGTH: 23
<212> TYPE: DNA
<213> ORGANISM: Artificial Sequence
<220> FEATURE:
<223> OTHER INFORMATION: G148N reverse primer

<400> SEQUENCE: 18
gaagttgaca gtgaaggctt ctg                                         23

<210> SEQ ID NO 19
<211> LENGTH: 21
<212> TYPE: DNA
<213> ORGANISM: Artificial Sequence
<220> FEATURE:
<223> OTHER INFORMATION: G148T forward primer

<400> SEQUENCE: 19
actgacaccg aagaggccaa g                                           21

<210> SEQ ID NO 20
<211> LENGTH: 23
<212> TYPE: DNA
<213> ORGANISM: Artificial Sequence
<220> FEATURE:
<223> OTHER INFORMATION: G148T reverse primer

<400> SEQUENCE: 20
gaagttgaca gtgaaggctt ctg                                         23

```
<210> SEQ ID NO 21
<211> LENGTH: 24
<212> TYPE: DNA
<213> ORGANISM: Artificial Sequence
<220> FEATURE:
<223> OTHER INFORMATION: R178N forward primer

<400> SEQUENCE: 21
aacgacacag tttttgctct ggtg                                          24

<210> SEQ ID NO 22
<211> LENGTH: 23
<212> TYPE: DNA
<213> ORGANISM: Artificial Sequence
<220> FEATURE:
<223> OTHER INFORMATION: R178N reverse primer

<400> SEQUENCE: 22
gtcaagctcc ttgaccaaat cca                                           23

<210> SEQ ID NO 23
<211> LENGTH: 21
<212> TYPE: DNA
<213> ORGANISM: Artificial Sequence
<220> FEATURE:
<223> OTHER INFORMATION: K201N forward primer

<400> SEQUENCE: 23
aacgacaccg aggaagagga c                                             21

<210> SEQ ID NO 24
<211> LENGTH: 23
<212> TYPE: DNA
<213> ORGANISM: Artificial Sequence
<220> FEATURE:
<223> OTHER INFORMATION: K201N reverse primer

<400> SEQUENCE: 24
gacttcaaag ggtctctccc att                                           23

<210> SEQ ID NO 25
<211> LENGTH: 21
<212> TYPE: DNA
<213> ORGANISM: Artificial Sequence
<220> FEATURE:
<223> OTHER INFORMATION: Q212N forward primer

<400> SEQUENCE: 25
aacgtgacca ccgtgaaggt g                                             21

<210> SEQ ID NO 26
<211> LENGTH: 21
<212> TYPE: DNA
<213> ORGANISM: Artificial Sequence
<220> FEATURE:
<223> OTHER INFORMATION: Q212N reverse primer

<400> SEQUENCE: 26
gtccacgtgg aagtcctctt c                                             21

<210> SEQ ID NO 27
<211> LENGTH: 23
<212> TYPE: DNA
<213> ORGANISM: Artificial Sequence
<220> FEATURE:
<223> OTHER INFORMATION: E266N forward primer
```

```
<400> SEQUENCE: 27
aacctcaccc acgatatcat cac                                              23

<210> SEQ ID NO 28
<211> LENGTH: 24
<212> TYPE: DNA
<213> ORGANISM: Artificial Sequence
<220> FEATURE:
<223> OTHER INFORMATION: E266N reverse primer

<400> SEQUENCE: 28
attttccagg tgctgtagtt tccc                                             24

<210> SEQ ID NO 29
<211> LENGTH: 16
<212> TYPE: DNA
<213> ORGANISM: Artificial Sequence
<220> FEATURE:
<223> OTHER INFORMATION: K343N forward primer

<400> SEQUENCE: 29
aacgggactg aagctg                                                      16

<210> SEQ ID NO 30
<211> LENGTH: 16
<212> TYPE: DNA
<213> ORGANISM: Artificial Sequence
<220> FEATURE:
<223> OTHER INFORMATION: K343N reverse primer

<400> SEQUENCE: 30
ctcgtcgatg gtcagc                                                      16

<210> SEQ ID NO 31
<211> LENGTH: 105
<212> TYPE: DNA
<213> ORGANISM: Artificial Sequence
<220> FEATURE:
<223> OTHER INFORMATION: A1AT forward primer 2

<400> SEQUENCE: 31
gggcccctcg aggccaccat gccgtcttct gtctcgtggg gcatcctcct gctggcaggc      60
ctgtgctgcc tggtccctgt ctccctggct gaagatcccc aggga                     105

<210> SEQ ID NO 32
<211> LENGTH: 30
<212> TYPE: DNA
<213> ORGANISM: Artificial Sequence
<220> FEATURE:
<223> OTHER INFORMATION: A1AT reverse primer 2

<400> SEQUENCE: 32 gggggatcc tcttttggg tgggattcac                                         30

<210> SEQ ID NO 33
<211> LENGTH: 36
<212> TYPE: DNA
<213> ORGANISM: Artificial Sequence
<220> FEATURE:
<223> OTHER INFORMATION: hGH forward primer

<400> SEQUENCE: 33
gggcccctcg aggccaccat ggctacaggc tcccgg                                36
```

```
<210> SEQ ID NO 34
<211> LENGTH: 30
<212> TYPE: DNA
<213> ORGANISM: Artificial Sequence
<220> FEATURE:
<223> OTHER INFORMATION: hGH reverse primer

<400> SEQUENCE: 34
ggggggatcc tcgaagccac agctgccctc                                    30

<210> SEQ ID NO 35
<211> LENGTH: 38
<212> TYPE: DNA
<213> ORGANISM: Artificial Sequence
<220> FEATURE:
<223> OTHER INFORMATION: P357N forward primer

<400> SEQUENCE: 35
ccatgttttt agaggccata aacatgtcta tccccccc                            38

<210> SEQ ID NO 36
<211> LENGTH: 38
<212> TYPE: DNA
<213> ORGANISM: Artificial Sequence
<220> FEATURE:
<223> OTHER INFORMATION: P357N reverse primer

<400> SEQUENCE: 36
gggggggata gacatgttta tggcctctaa aaacatgg                            38

<210> SEQ ID NO 37
<211> LENGTH: 30
<212> TYPE: DNA
<213> ORGANISM: Artificial Sequence
<220> FEATURE:
<223> OTHER INFORMATION: XhoCSF forward primer

<400> SEQUENCE: 37
gggcccctcg agatggctgg acctgccacc                                    30

<210> SEQ ID NO 38
<211> LENGTH: 30
<212> TYPE: DNA
<213> ORGANISM: Artificial Sequence
<220> FEATURE:
<223> OTHER INFORMATION: CSFBam reverse primer

<400> SEQUENCE: 38
ggggggatcc tcgggctggg caaggtggcg                                    30

<210> SEQ ID NO 39
<211> LENGTH: 1182
<212> TYPE: DNA
<213> ORGANISM: Artificial Sequence
<220> FEATURE:
<223> OTHER INFORMATION: pT003

<400> SEQUENCE: 39
gaggatcccc agggagatgc tgcccagaag acagatacat cccaccatga tcaggatcac    60
ccaaccttca acaagatcac ccccaacctg gctgagttcg ccttcagcct ataccgccag   120
ctggcacacc agtccaacag caccaatatc ttcttctccc cagtgagcat cgctacagcc   180
tttgcaatgc tctccctggg gaccaaggct gacactcacg atgaaatcct ggagggcctg   240
aatttcaacc tcacggagat tccggaggct cagatccatg aaggcttcca ggaactcctc   300
```

```
cgtaccctca accagccaga cagccagctc cagctgacca ccggcaatgg cttgttcctc    360
agcgagggcc tgaagctagt ggataagttt ttggaggatg ttaaaaagtt gtaccactca    420
gaagccttca ctgtcaactt cggggacacc gaagaggcca agaaacagat caacgattac    480
gtggagaagg gtactcaagg gaaaattgtg gatttggtca aggagcttga cagagacaca    540 gttttgctc tggtgaatta catcttcttt aaaggcaaat gggagagacc ctttgaagtc    600
aaggacaccg aggaagagga cttccacgtg gaccaggtga ccaccgtgaa ggtgcctatg    660
atgaagcgtt taggcatgtt taacatccag cactgtaaga agctgtccag ctgggtgctg    720
ctgatgaaat acctgggcaa tgccaccgcc atcttcttcc tgcctgatga ggggaaacta    780
cagcacctgg aaaatgaact cacccacgat atcatcacca agttcctgga aaatgaagac    840
agaaggtctg ccagcttaca tttacccaaa ctgtccatta ctggaaccta tgatctgaag    900
agcgtcctgg gtcaactggg catcactaag gtcttcagca atgggctga cctctccggg     960 gtcacagagg aggcacccct gaagctctcc aaggccgtgc ataaggctgt gctgaccatc   1020
gacgagaaag ggactgaagc tgctggggcc atgtttttag aggccatacc catgtctatc   1080 cccccgagg tcaagttcaa caaaccctt gtcttcttaa tgattgacca aaataccaag    1140
tctcccctct tcatgggaaa agtggtgaat cccacccaaa aa                     1182

<210> SEQ ID NO 40
<211> LENGTH: 1182
<212> TYPE: DNA
<213> ORGANISM: Artificial Sequence
<220> FEATURE:
<223> OTHER INFORMATION: pT006

<400> SEQUENCE: 40
gaggatcccc aggagatgc tgcccagaag acagatacat cccaccatga tcaggatcac     60
ccaaccttca acaagatcac ccccaacctg gctgagttcg ccttcagcct ataccgccag    120
ctggcacacc agtccaacag caccaatatc ttcttctccc cagtgagcat cgctacagcc    180
tttgcaatgc tctccctggg gaccaaggct gacactcacg atgaaatcct ggagggcctg    240
aatttcaacc tcacggagat tccggaggct cagatccatg aaggcttcca ggaactcctc    300
cataccctca accagccaga cagccagctc cagctgacca ccggcaatgg cctgttcctc    360
agcgagggcc tgaagctagt ggataagttt ttggaggatg ttaaaaagtt gtaccactca    420
gaagccttca ctgtcaactt cggggacacc gaagaggcca agaaacagat caacgattac    480
gtggagaagg gtactcaagg gaaaattgtg gatttggtca aggagcttga cagagacaca    540 gttttgctc tggtgaatta catcttcttt aaaggcaaat gggagagacc ctttgaagtc    600
aaggacaccg aggaagagga cttccacgtg gaccaggtga ccaccgtgaa ggtgcctatg    660
atgaagcgtt taggcatgtt taacatccag cactgtaaga agctgtccag ctgggtgctg    720
ctgatgaaat acctgggcaa tgccaccgcc atcttcttcc tgcctgatga ggggaaacta    780
cagcacctgg aaaatgaact cacccacgat atcatcacca agttcctgga aaatgaagac    840
agaaggtctg ccagcttaca tttacccaaa ctgtccatta ctggaaccta tgatctgaag    900
agcgtcctgg gtcaactggg catcactaag gtcttcagca atgggctga cctctccggg     960 gtcacagagg aggcacccct gaagctctcc aaggccgtgc ataaggctgt gctgaccatc   1020
gacgagaaag ggactgaagc tgctggggcc atgtttttag aggccatacc catgtctatc   1080 cccccgagg tcaagttcaa caaaccctt gtcttcttaa tgattgacca aaataccaag    1140
tctcccctct tcatgggaaa agtggtgaat cccacccaaa aa                     1182
```

<210> SEQ ID NO 41
<211> LENGTH: 394
<212> TYPE: PRT
<213> ORGANISM: Artificial Sequence
<220> FEATURE:
<223> OTHER INFORMATION: Alpha-1 antitrypsine

<400> SEQUENCE: 41

```
Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365
```

```
Pro Phe Val Phe Leu Met Ile Asp Gln Asn Thr Lys Ser Pro Leu Phe
        370                 375                 380

Met Gly Lys Val Val Asn Pro Thr Gln Lys
385                 390
```

<210> SEQ ID NO 42
<211> LENGTH: 394
<212> TYPE: PRT
<213> ORGANISM: Artificial Sequence
<220> FEATURE:
<223> OTHER INFORMATION: Alpha-1 antitrypsine variant

<400> SEQUENCE: 42

```
Glu Asp Pro Gln Gly Asp Ala Ala Asn Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335
```

Val Leu Thr Ile Asp Glu Lys Gly Thr Glu Ala Ala Gly Ala Met Phe
                340                 345                 350

Leu Glu Ala Ile Pro Met Ser Ile Pro Pro Glu Val Lys Phe Asn Lys
            355                 360                 365

Pro Phe Val Phe Leu Met Ile Asp Gln Asn Thr Lys Ser Pro Leu Phe
    370                 375                 380

Met Gly Lys Val Val Asn Pro Thr Gln Lys
385                 390

<210> SEQ ID NO 43
<211> LENGTH: 1755
<212> TYPE: DNA
<213> ORGANISM: Artificial Sequence
<220> FEATURE:
<223> OTHER INFORMATION: phGH-AT9N DNA

<400> SEQUENCE: 43

| | | | | | |
|---|---|---|---|---|---|
| ttcccaacca | ttcccttatc | caggcttttt | gacaacgcta | tgctccgcgc | ccatcgtctg | 60 |
| caccagctgg | cctttgacac | ctaccaggag | tttgaagaag | cctatatccc | aaaggaacag | 120 |
| aagtattcat | tcctgcagaa | cccccagacc | tccctctgtt | tctcagagtc | tattccgaca | 180 |
| ccctccaaca | gggaggaaac | acaacagaaa | tccaacctag | agctgctccg | catctccctg | 240 |
| ctgctcatcc | agtcgtggct | ggagcccgtg | cagttcctca | ggagtgtctt | cgccaacagc | 300 |
| ctggtgtacg | gcgcctctga | cagcaacgtc | tatgacctcc | taaaggacct | agaggaaggc | 360 |
| atccaaacgc | tgatggggag | ctggaagat | ggcagccccc | ggactgggca | gatcttcaag | 420 |
| cagacctaca | gcaagttcga | cacaaactca | cacaacgatg | acgcactact | caagaactac | 480 |
| gggctgctct | actgcttcag | gaaggacatg | gacaaggtcg | agacattcct | gcgcatcgtg | 540 |
| cagtgccgct | ctgtggaggg | cagctgtggc | ttcgaggatc | cccagggaga | tgctgccaac | 600 |
| aagacagata | catcccacca | tgatcaggat | cacccaacct | tcaacaagat | cacccccaac | 660 |
| ctggctgagt | cgccttcag | cctataccgc | cagctggcac | accagtccaa | cagcaccaat | 720 |
| atcttcttct | ccccagtgag | catcgctaca | gcctttgcaa | tgctctccct | ggggaccaag | 780 |
| gctgacactc | acgatgaaat | cctggagggc | ctgaatttca | acctcacgga | gattccggag | 840 |
| gctcagatcc | atgaaggctt | ccaggaactc | ctccataccc | tcaaccagcc | agacagccag | 900 |
| ctccagctga | ccaccggcaa | tggcctgttc | ctcagcgagg | cctgaagct | agtggataag | 960 |
| tttttggagg | atgttaaaaa | gttgtaccac | tcagaagcct | tcactgtcaa | cttcggggac | 1020 |
| accgaagagg | ccagaaaaca | gatcaacgat | tacgtggaga | agggtactca | agggaaaatt | 1080 |
| gtggatttgg | tcaaggagct | tgacagagac | acagttttg | ctctggtgaa | ttacatcttc | 1140 |
| tttaaaggca | atggggagag | ccctttgaa | gtcaaggaca | ccgaggaaga | ggacttccac | 1200 |
| gtggaccagg | tgaccaccgt | gaaggtgcct | atgatgaagc | gtttaggcat | gtttaacatc | 1260 |
| cagcactgta | agaagctgtc | cagctgggtg | ctgctgatga | ataccctggg | caatgccacc | 1320 |
| gccatcttct | tcctgcctga | tgaggggaaa | ctacagcacc | tggaaaatga | actcacccac | 1380 |
| gatatcatca | ccaagttcct | ggaaaatgaa | gacagaaggt | ctgccagctt | acatttaccc | 1440 |
| aaactgtcca | ttactggaac | ctatgatctg | aagagcgtcc | tgggtcaact | gggcatcact | 1500 |
| aaggtcttca | gcaatggggc | tgacctctcc | ggggtcacag | aggaggcacc | cctgaagctc | 1560 |
| tccaaggccg | tgcataaggc | tgtgctgacc | atcgacgaga | aagggactga | agctgctggg | 1620 |
| gccatgtttt | tagaggccat | acccatgtct | atccccccg | aggtcaagtt | caacaaaccc | 1680 |

```
tttgtcttct taatgattga ccaaaatacc aagtctcccc tcttcatggg aaaagtggtg    1740
aatcccaccc aaaaa                                                    1755
```

<210> SEQ ID NO 44
<211> LENGTH: 394
<212> TYPE: PRT
<213> ORGANISM: Artificial Sequence
<220> FEATURE:
<223> OTHER INFORMATION: Alpha-1 antitrypsine divariant

<400> SEQUENCE: 44

```
Glu Asp Pro Gln Gly Asp Ala Ala Asn Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Glu Gly Leu Lys Leu Val Asp
        115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350
```

Leu Glu Ala Ile Asn Met Ser Ile Pro Pro Glu Val Lys Phe Asn Lys
        355                 360                 365

Pro Phe Val Phe Leu Met Ile Asp Gln Asn Thr Lys Ser Pro Leu Phe
        370                 375                 380

Met Gly Lys Val Val Asn Pro Thr Gln Lys
385                 390

<210> SEQ ID NO 45
<211> LENGTH: 1706
<212> TYPE: DNA
<213> ORGANISM: Artificial Sequence
<220> FEATURE:
<223> OTHER INFORMATION: pT603N

<400> SEQUENCE: 45

| | | | | | |
|---|---|---|---|---|---|
| ccaccccct | gggccctgcc | agctccctgc | cccagagctt | cctgctcaag tgcttagagc | 60 |
| aagtgaggaa | gatccagggc | gatggcgcag | cgctccagga | gaagctgtgt gccacctaca | 120 |
| agctgtgcca | ccccgaggag | ctggtgctgc | tcggacactc | tctgggcatc ccctgggctc | 180 |
| ccctgagcag | ctgccccagc | caggccctgc | agctggcagg | ctgcttgagc caactccata | 240 |
| gcggcctttt | cctctaccag | gggctcctgc | aggccctgga | agggatctcc cccgagttgg | 300 |
| gtcccacctt | ggacacactg | cagctggacg | tcgccgactt | tgccaccacc atctggcagc | 360 |
| agatggaaga | actgggaatg | gcccctgccc | tgcagcccac | ccagggtgcc atgccggcct | 420 |
| tcgcctctgc | tttccagcgc | cgggcaggag | gggtcctggt | tgcctcccat ctgcagagct | 480 |
| tcctggaggt | gtcgtaccgc | gttctacgcc | accttgccca | gccgaggat ccccaggag | 540 |
| atgctgccaa | caagacagat | acatcccacc | atgatcagga | tcacccaacc ttcaacaaga | 600 |
| tcaccccccaa | cctggctgag | ttcgccttca | gcctataccg | ccagctggca caccagtcca | 660 |
| acagcaccaa | tatcttcttc | tccccagtga | gcatcgctac | agcctttgca atgctctccc | 720 |
| tggggaccaa | ggctgacact | cacgatgaaa | tcctggaggg | cctgaatttc aacctcacgg | 780 |
| agattccgga | ggctcagatc | catgaaggct | tccaggaact | cctccatacc ctcaaccagc | 840 |
| cagacagcca | gctccagctg | accaccggca | atggcctgtt | cctcagcgag ggcctgaagc | 900 |
| tagtggataa | gtttttggag | gatgttaaaa | agttgtacca | ctcagaagcc ttcactgtca | 960 |
| acttcgggga | caccgaagag | gccaagaaac | agatcaacga | ttacgtggag aagggtactc | 1020 |
| aagggaaaat | tgtggatttg | gtcaaggagc | ttgacagaga | cacagttttt gctctggtga | 1080 |
| attacatctt | ctttaaaggc | aaatgggaga | gaccctttga | agtcaaggac accgaggaag | 1140 |
| aggacttcca | cgtggaccag | gtgaccaccg | tgaaggtgcc | tatgatgaag cgtttaggca | 1200 |
| tgtttaacat | ccagcactgt | aagaagctgt | ccagctgggt | gctgctgatg aaatacctgg | 1260 |
| gcaatgccac | cgccatcttc | ttcctgcctg | atgaggggaa | actacagcac ctggaaaatg | 1320 |
| aactcaccca | cgatatcatc | accaagttcc | tggaaaatga | agacagaagg tctgccagct | 1380 |
| tacatttacc | caaactgtcc | attactggaa | cctatgatct | gaagagcgtc ctgggtcaac | 1440 |
| tgggcatcac | taaggtcttc | agcaatgggg | ctgacctctc | cggggtcaca gaggaggcac | 1500 |
| ccctgaagct | ctccaaggcc | gtgcataagg | ctgtgctgac | catcgacgag aaagggactg | 1560 |
| aagctgctgg | ggccatgttt | ttagaggcca | taaacatgtc | tatcccccc gaggtcaagt | 1620 |
| tcaacaaacc | ctttgtcttc | ttaatgattg | accaaaatac | caagtctccc ctcttcatgg | 1680 |
| gaaaagtggt | gaatcccacc | caaaaa | | | 1706 |